(12) United States Patent
Cline et al.

(10) Patent No.: US 7,857,796 B2
(45) Date of Patent: Dec. 28, 2010

(54) OSTOMY APPLIANCE HAVING PRESSURE APPLYING MEMBER

(75) Inventors: John B. Cline, New Brunswick, NJ (US); Tinh Nguyen DeMary, Milltown, NJ (US); Andrew M. Lovatt, Cambridgeshire (GB); Philip A. Davies, Cambridgeshire (GB); Paul A. Johnson, Cambridgeshire (GB); Gary Stacey, Cambridgeshire (GB); Iain Ansell, Suffolk (GB)

(73) Assignee: Bristol-Myers Squibb Company, New York, NY (US)

( * ) Notice: Subject to any disclaimer, the term of this patent is extended or adjusted under 35 U.S.C. 154(b) by 159 days.

(21) Appl. No.: 12/022,335

(22) Filed: Jan. 30, 2008

(65) Prior Publication Data
US 2008/0119804 A1 May 22, 2008

Related U.S. Application Data

(60) Division of application No. 10/397,928, filed on Mar. 26, 2003, now Pat. No. 7,347,844, which is a continuation-in-part of application No. 10/107,998, filed on Mar. 27, 2002, now Pat. No. 6,723,079.

(51) Int. Cl.
*A61F 5/44* (2006.01)
(52) U.S. Cl. .............. 604/338; 604/332; 604/333; 604/334; 604/335; 604/336; 604/337; 604/339; 604/340; 604/341; 604/342; 604/344; 604/345; 604/355; 604/277; 600/29; 600/30; 600/31; 600/32
(58) Field of Classification Search ......... 604/332–345, 604/355, 277; 600/29–32
See application file for complete search history.

(56) References Cited

U.S. PATENT DOCUMENTS

| 3,970,085 | A | | 7/1976 | Mersan |
| 4,233,977 | A | | 11/1980 | Mattson |
| 4,950,223 | A | * | 8/1990 | Silvanov ............ 600/32 |
| 5,004,464 | A | | 4/1991 | Leise |
| 5,195,996 | A | * | 3/1993 | Edwards et al. ........ 604/338 |
| 5,312,384 | A | | 5/1994 | Temple |
| 5,667,502 | A | | 9/1997 | Holtermann |

(Continued)

FOREIGN PATENT DOCUMENTS

EP 1 348 411 A1 * 10/2003

(Continued)

*Primary Examiner*—Tatyana Zalukaeva
*Assistant Examiner*—Ginger T Chapman
(74) *Attorney, Agent, or Firm*—Stuart E. Krieger

(57) ABSTRACT

An ostomy appliance is described in the form of a controlled discharge device for controlling discharge from the stoma and/or an ostomy pouch for collecting discharged waste. The appliance may include one or more of: an elastomeric stoma seal for providing a seal around or directly against the stoma; a stoma occluder for occluding the stoma without passing internally into the stoma; a peristomal foam wall; a confinement seal for confining at least solid excreta to a confinement region adjacent to the stoma; a stowable collector bag; and interchangeable controlled discharge devices and ostomy pouches. The foam wall may provide a barrier to stool, but allow escape of flatus. The foam wall and/or the stoma occluder and/or the confinement seal may apply a force in a direction to increase the sealing force on the stoma seal.

21 Claims, 26 Drawing Sheets

U.S. PATENT DOCUMENTS

| | | |
|---|---|---|
| 6,071,268 A | 6/2000 | Wagner |
| 6,689,111 B2 * | 2/2004 | Mulhauser et al. .......... 604/332 |
| 6,740,067 B2 | 5/2004 | Leise |
| 2003/0088219 A1 | 5/2003 | Metz |
| 2006/0206069 A1 | 9/2006 | Cline |

FOREIGN PATENT DOCUMENTS

| | | |
|---|---|---|
| EP | 1 348 412 A1 * | 10/2003 |
| GB | 751333 | 6/1956 |
| WO | WO9218074 | 10/1992 |

* cited by examiner

OSTOMY APPLIANCE HAVING PRESSURE APPLYING MEMBER

This application is a divisional of U.S. application Ser. No. 10/397,928 filed, Mar. 26, 2003 now U.S. Pat. No. 7,347,844, which is a continuation-in-part of U.S. application Ser. No. 10/107,998 filed, Mar. 27, 2002, now U.S. Pat. No. 6,723,079 issued on Apr. 20, 2004, and which are hereby incorporated by reference in their entirety. This application claims the benefit of priority from U.S. application Ser. No. 10/107,998, filed Mar. 27, 2002.

FIELD OF THE INVENTION

The present invention relates to an ostomy appliance to be worn by an ostomate. The invention may be applied to a mounting device (e.g. a faceplate) for securing a collection pouch to a stoma, or to a controlled discharge device for controlling or restricting discharge from the stoma. In particular, the invention may relate to various forms of seal in the region of the stoma.

BACKGROUND TO THE INVENTION

One aspect of the invention may relate to an ostomy appliance in the form of a controlled discharge device, for controlling or at least restricting discharge from the stoma. Such a device may also be referred to as an ostomy or stoma "port". A conventional controlled discharge device typically comprises a plug or bung insertable into the stoma (or into a socket itself received within the stoma) to block the stoma internally. When the ostomate desires to pass waste the plug or bung is manually removed. A variation of this design comprises a fixed socket inserted into the stoma, the socket including an inflatable balloon for blocking the waste passage in the socket internally. Blocking the stoma internally is seen as essential to produce the most effective seal against the pressure of body waste. However, such conventional devices have not earned significant acceptance or confidence among ostomates. Although a controlled discharge device potentially offers an ostomate more personal control of his or her discharges of body waste, and may alleviate the burden of wearing a waste collection pouch, it is believed that doubts remain among ostomates about the comfort, hygiene, effectiveness, and potential invasive effects, of an internally fitting stoma device.

Another aspect of the invention may relate to a sealing member for providing a seal around the stoma. Sealing against or around the stoma is difficult. As well as being comfortable for the ostomate to wear, any seal must not exert too high a pressure on the stoma. Too high a pressure may damage the stoma, and prevent blood flow to the tissue. Various moldable and non-moldable sealing members have been proposed in the art, but this aspect of the invention may relate to a substantially non-moldable, elastomeric sealing member. The term "non-moldable" may mean that the sealing member is not easily plastically deformable when in use, in contrast to a moldable sealing member which is intended to be manually shaped by the ostomate in use. For example, U.S. 60/071268 describes an ostomy faceplate including a pad of a barrier adhesive, a non-moldable sealing ring of silicon foam, and a blotter-ring disposed between the pad and the sealing ring. The sealing ring is provided by a soft elastomeric doughnut (or other convex cross-section profile) which sits laterally (radially) outside the stoma to provide a gentle, laterally acting, O-ring type seal contacting the stoma. A potential disadvantage of such a seal is that the seal area is relatively limited. The seal may be relatively weak and vulnerable to leakage when contacted by human waste for extended periods of time, or under significant waste pressure (for example, in a controlled discharge device).

SUMMARY OF THE INVENTION

Referring to the combination diagram of FIG. 1, the invention proposes a number of features, each novel and advantageous in itself. The features may be used in an ostomy appliance either in isolation or in combination, to achieve different effects. The features include one or more of:

A: an elastomeric seal for providing a seal around or against the stoma;

B: a non-entrant stoma occluder for occluding the stoma externally. The terms "non-entrant" and "external" may generally mean that the occluder does not pass internally into the stoma;

C: a peristomal foam wall;

D: a confinement volume seal;

E: an interchangeable ostomy pouch and controlled discharge device; and

F: a controlled discharge device incorporating a stowed discharge collector.

A: Elastomeric Stoma Seal

Broadly speaking, a first aspect of the invention may provide a sealing member at least a portion of which is elastomeric. The sealing member may be configured for sealing around or against a stoma. The sealing member may have a closed loop shape.

The sealing member (or at least the elastomeric portion) may be substantially non-moldable (for example, meaning that it cannot easily be reshaped plastically by manual deformation). A substantially non-moldable sealing member is preferred to reduce the possibility that the sealing member may lose sealing force or integrity by substantial plastic deformation (for example, when body waste is pressed against the sealing member for an extended period or at high pressure).

The sealing member may be used in combination with an adhesive wafer for securing an ostomy appliance to the wearer's skin. The sealing member may be configured to seal a periphery of a stomal aperture in the adhesive wafer. The sealing member may at least partly overlap the adhesive at the stomal aperture of the wafer, and/or the sealing member may be received at least partly in a gap between the adhesive and the stoma.

The sealing member may protect the adhesive wafer from exposure to stomal discharge and/or prevent (or at least obstruct) leakage of stomal discharge between the adhesive and the skin. Such protection may be especially advantageous for an ostomy appliance to be worn for an extended period of time, or to be subjected to stomal discharge at high pressure (for example, a controlled discharge device).

The sealing member may be configured to contact the body to form a seal against the body. The sealing member may be configured to contact a portion of the stoma and/or to contact skin around the stoma (e.g., peristomal skin). The sealing member may be configured not to contact the stoma. Alternatively, the sealing member may be configured to contact the stoma.

The sealing member may of an impermeable material and/or have an impermeable surface.

In one form, the sealing member may be in the form of a gasket for at least partly overlapping the stoma. The sealing member may be configured to apply sealing pressure to the stoma at least partly in an axial direction (for example, at least partly in a direction perpendicular to the skin surface).

Additionally or alternatively, the sealing member may preferably have a stoma engaging surface with a generally closed-loop concave configuration. The term "concave" may be used broadly to mean that the stoma engaging surface is dished or has a taper or flare such that the sealing member may at least partly cup the surface of the stoma. Such an arrangement can increase the seal area and effectiveness. The sealing member may be profiled to have the concave configuration as its natural shape, or the sealing member may have a different natural shape and deform in use to adopt the concave configuration. For example, the stoma engaging portion of the sealing member may be flat or planar in an unstressed condition, but deform to provide the concave configuration when fitted to or around the stoma.

The stoma engaging surface (if provided) may be configured to engage up to about one third of the height (or protruding height) of the stoma, in use.

The sealing member may be shaped or supported to apply sealing pressure to the peristomal skin around the stoma. A greater sealing force may be applied peristomally than could be applied to the stoma, without the same problems of comfort and stoma damage. Such peristomal pressure can improve the seal performance, for example, by one or more of: increasing the area against which the seal can be made; and application of a sealing force to the peristomal skin surrounding the stoma. The applied pressure may also tend to at partly increase the degree of protuberance of the stoma, at least relative to the region of skin to which pressure is applied. If the sealing member includes a stoma contacting surface, increasing the protuberance of the stoma can provide greater stoma area to be contacted (e.g., cupped) by the sealing member and can also urge the stoma outwardly into engagement with the stoma contacting surface of the sealing member.

Means may be provided for directly or indirectly applying pressure to the sealing member to urge the sealing member against the stoma and/or peristomal skin. Such pressure applying means may, for example, comprise one or more of: a convex shape defining member; a resilient pressure applying member; an inflatable (or pre-inflated) member; a resiliently compressible material, such as foam. The pressure applying means may apply pressure directly or indirectly to a surface of the sealing member facing away from the skin.

The sealing member can also be configured or supported so as to apply greater sealing force around the outside of the stoma (e.g., peristomally) than to the stoma surface itself. This may help protect the stoma from excessive force, while still allowing a high sealing force to be used peristomally.

As an alternative to the sealing member acting peristomally, another portion of the ostomy appliance may be configured for applying pressure to the peristomal skin around the stoma. With such an arrangement, the seal member may still benefit from the above described effects of increasing stoma protuberance.

The elastomeric portion of the sealing member may be made of any suitable material, for example, natural or synthetic rubber, silicone, or foam. Such materials may provide excellent cushioning properties (e.g., for comfort), at the same time as excellent elastomeric conformity (e.g., to achieve a closely fitting seal).

In one form, the sealing member may be of a composite construction, comprising first and second materials. A first material may provide an impermeable elastomeric sealing surface for contacting with the peristomal skin and/or stoma, to prevent leakage of stomal discharge. A second material may provide a foam ring, for example, of open cell foam. The foam material may obstruct release of solid and liquid discharge, but permit escape of flatus gas. The foam material may have one or more properties of the peristomal foam wall described below. The first and second materials may form a unitary seal member, or the first and second materials may be separable elements.

The sealing member may be used in a conventional ostomy faceplate for sealing around the stoma, for example, to prevent waste matter from contacting the peristomal skin or from eroding an adhesive attaching the appliance to the skin. The excellent sealing performance of the elastomeric sealing member may also be especially suitable for use in a controlled discharge ostomy appliance for controlling or restricting discharge from the stoma. Preferably, the controlled discharge device is a non-entrant device which does not enter the stoma. The sealing member can provide significant advantages in achieving a high integrity seal around the stoma to prevent leakage when the device acts to prevent or restrict stomal discharge.

B: Non-Entrant Stoma Occluder

Broadly speaking, a second aspect of the invention provides a stoma occluder that acts externally, without entering the stoma itself.

The stoma occluder may, for example, be implemented as a membrane or drape at least partly covering the stoma. The membrane or drape may be formed by a sheet. Alternatively, the stoma occluder may be implemented as a block, pad or wad of material.

The stoma occluder may be pressed against the stoma, for providing a sealing force for occluding the stoma externally. In one form, the stoma occluder may be implemented as, or supported by, an inflatable or inflated device. The term "inflatable/inflated" may be used broadly to mean any device that can be/is expanded, supported or extended by fluid pressure. The inflatable/inflated device may be inflated using any suitable inflation fluid, for example, a liquid (e.g., saline) or gas (e.g., air). The stoma occluder may be pressed against the stoma by the pressure of inflation. Implementing the stoma occluder as an inflatable member has an advantage that the fluid can provide a substantially uniform application of pressure as the occluder adapts to the shape of the stoma, regardless of the stoma shape or non-uniformities in the stoma shape.

The inflatable device may include an inflation port through which the device is inflated. Additionally or alternatively, the inflatable device may be pre-inflated (for example, during manufacture or packaging) and supplied to a user as a ready-inflated item. The inflation pressure may be regulated by a feature of the appliance that determines the volume of the inflatable device. For example, the feature may be the distance between the stoma and a support surface of the appliance that supports or contacts the inflatable device. The distance may be controlled by one or more spacers, or by a height adjusting mechanism, or a characteristic dimension of the appliance. A plurality of appliances may be provided having different characteristic dimensions, to provide different inflation pressures. An ostomate may select or be prescribed a specific appliance to suit his or her stoma.

In an alternative form, the stoma occluder may be implemented as, or supported by, an elastomeric member. For example, the occluder may be of, or supported by, a resiliently compressible material, such as foam. Soft foam can provide excellent elastomeric conformity to adapt to the shape of an individual's stoma and, at the same time, provide excellent cushioning properties for a comfortable fit.

A hybrid occluder including both an inflatable/inflated device and a foam member is also envisaged.

The stoma occluder may be impermeable, partly permeable, or substantially permeable, depending on the desired barrier properties for solid waste (stool), liquid waste and gas waste components.

The stoma occluder may have a generally planar surface, or it may be profiled to fit (either approximately or exactly) a stoma.

The stoma occluder is especially, but not exclusively, suitable for a controlled discharge device ostomy appliance.

C: Peristomal Foam Wall

Broadly speaking, a third aspect of the present invention provides a wall extending peristomally, and comprising foam.

Preferably, the wall is of a closed-loop configuration. The wall may define at least partly a confinement region for confining any solid waste excreted from the stoma. The wall may be made of or comprise foam material.

In one form, the wall may comprise open cell foam for permitting flatus to vent therethrough. The open cell foam may act as a separator for separating flatus gas from solid and/or semi-solid and/or liquid body waste. Solid body waste may generally not be able to pass through the foam. Liquid and/or semi-solid waste may soak into the foam, but may in general be obstructed in passing through the foam cells by the surface tension of the liquid.

In one form, the wall may be of resiliently compressible foam. In use, the foam may be compressed, for producing a tight seal between first and second separable parts of the appliance. The compressed foam is able to ensure a strong seal around the confinement region.

Additionally or alternatively, compression of resilient foam may be used to apply a force to a sealing member. For example, the sealing member may be configured for sealing around or against the stoma, and/or for sealing an inner periphery in a stomal aperture of the appliance. The sealing member may be the elastomeric foam seal described hereinbefore. In one form, the compressed foam wall may apply pressure directly or indirectly to at least a peristomal region of the sealing member. The foam wall may be unitary with the sealing member, or the two may be separate or separable elements.

The wall may be secured to at least one of a faceplate and a cover.

The wall may be especially suitable for use in a controlled discharge device for controlling or at least obstructing the discharge of body waste from the stoma. The wall may be especially advantageous in combination with one or more of: the elastomeric stoma seal; the non-entrant stoma occluder; and a confinement volume seal described below.

D: Confinement Volume Seal

Broadly speaking, a fourth aspect of the invention provides a seal for defining at least partly a confinement volume, for example, in a controlled discharge device. The confinement volume is a volume external to the stoma, within which stomal discharge (other than flatus) may be substantially confined. Flatus may be vented.

The confinement volume seal may be effective between a first portion of the appliance that is releasably mounted with respect to a second portion of the appliance. The confinement seal may at least partly define the confinement volume when the first portion is mounted with respect to the second portion. The confinement volume seal may be broken by releasing the first portion from the second portion.

The confinement volume seal may be formed at least partly by, or include, one or more of the elastomeric sealing member, the foam wall, and the non-entrant stoma occluder. Additionally or alternatively, a closed loop (e.g. toroidal) confinement member may be provided for applying pressure in a direction towards the skin. The confinement member may be configured not to apply pressure to the stoma. Instead, the confinement member may be configured to apply pressure to the foam wall and/or the elastomeric sealing member, to increase the sealing effect surrounding the stoma.

The confinement member may be an inflatable or inflated member. As before, the term "inflatable/inflated" may be used broadly to mean any device that can be/is expanded, supported or extended by fluid pressure. The confinement member may include an inflation port through which the device is inflated. Additionally or alternatively, the confinement device may be pre-inflated (for example, during manufacture or packaging) and supplied to a user as a ready-inflated item. The inflation pressure may be regulated by a feature of the appliance that determines the volume of the confinement member. For example, the feature may be the distance between a surface against which the confinement members bears, and a support surface of the appliance that supports the confinement member. The distance may be controlled by one or more spacers, or by a height adjusting mechanism, or a characteristic dimension of the appliance. A plurality of appliances may be provided having different characteristic dimensions, to provide different inflation pressures. An ostomate may select or be prescribed a specific appliance to suit his or her stoma.

In another form, the confinement member may comprise an elastomeric material to provide a sealing pressure. Alternatively, the confinement member could be a composite construction including a spring element (e.g. of metal or plastics) enclosed by an impermeable material.

In a preferred form, a foam wall ring may be arranged between the confinement member and the peristomal skin. The foam wall ring may have one or more properties of the peristomal foam wall described above. The foam material may be compressed by the pressure applied by the confinement member. The properties of the foam and the amount of compression may be configured to prevent escape of solid and liquid components of stomal discharge, while allow flatus gas to escape through the foam.

Additionally or alternatively, an elastomeric sealing member may be arranged for sealing around and/or against the stoma. The elastomeric sealing member may have one or more properties of the elastomeric sealing member described above. The elastomeric sealing member may be a resilient, conformable member that may create a seal against or around the base of the stoma, to prevent exposure of an adhesive wafer to stomal discharge.

E. Interchangeable Ostomy Pouch and Controlled Discharge Device.

Broadly speaking, a fifth aspect of the invention generally provides a universal adhesive faceplate comprising a coupling means for mounting selectively either an ostomy pouch, or a controlled discharge device, to the universal faceplate.

The controller discharge device may be non-entrant, such that the controlled discharge device does not enter the stoma.

The coupling means on the faceplate may be configured to permit releasable attachment of the ostomy pouch or controlled discharge device to the faceplate. The faceplate may remain in situ on the wearer's skin while one device is interchanged for the other. This can allow an ostomate to swap between an ostomy pouch and a controlled discharge device without having to replace an adhesive faceplate. The inconvenience of removing an existing adhesive faceplate, and applying a new adhesive faceplate unnecessarily, can therefore be avoided.

F. A Controlled Discharge Device Incorporation a Stowed Discharge Collector

Broadly speaking, a sixth aspect of the invention generally provides a controlled discharge device which incorporates a stowed collector for collecting stomal discharge.

The controlled discharge device may comprise a first member, a second member releasably secured (or securable) to the first member, and a collapsible collector coupled between the first and second members. In an operative (secured) position of the first and second members for preventing (or at least limiting) stomal discharge, the collector may be collapsed to a stowed condition in which the collector occupies only a small volume. For example, the collector may be collapsed accordion-style, or folded on itself. The collapsed collector may be stowed within the appliance.

When the second member is released from the first member, the collector may be distended, to define a larger collection volume for collecting exudate from the stoma. This permits body waste to be discharged when desired by the ostomate, and collected hygienically without having to interchange a collection pouch for the controlled discharge device in order to collect body waste discharged immediately following unblocking of the stoma.

Although certain features and aspects of the invention have been highlighted above, the invention is not limited to these features. The Applicant claims protection for any novel feature, combination of features, or idea, described herein and/or illustrated in the drawings whether or not emphasis has been placed thereon.

BRIEF DESCRIPTION OF THE DRAWINGS

Non-limiting preferred embodiments are now described by way of example only, with reference to the accompanying schematic drawings, in which.

DETAILED DESCRIPTION OF PREFERRED EMBODIMENTS

Figure 1:
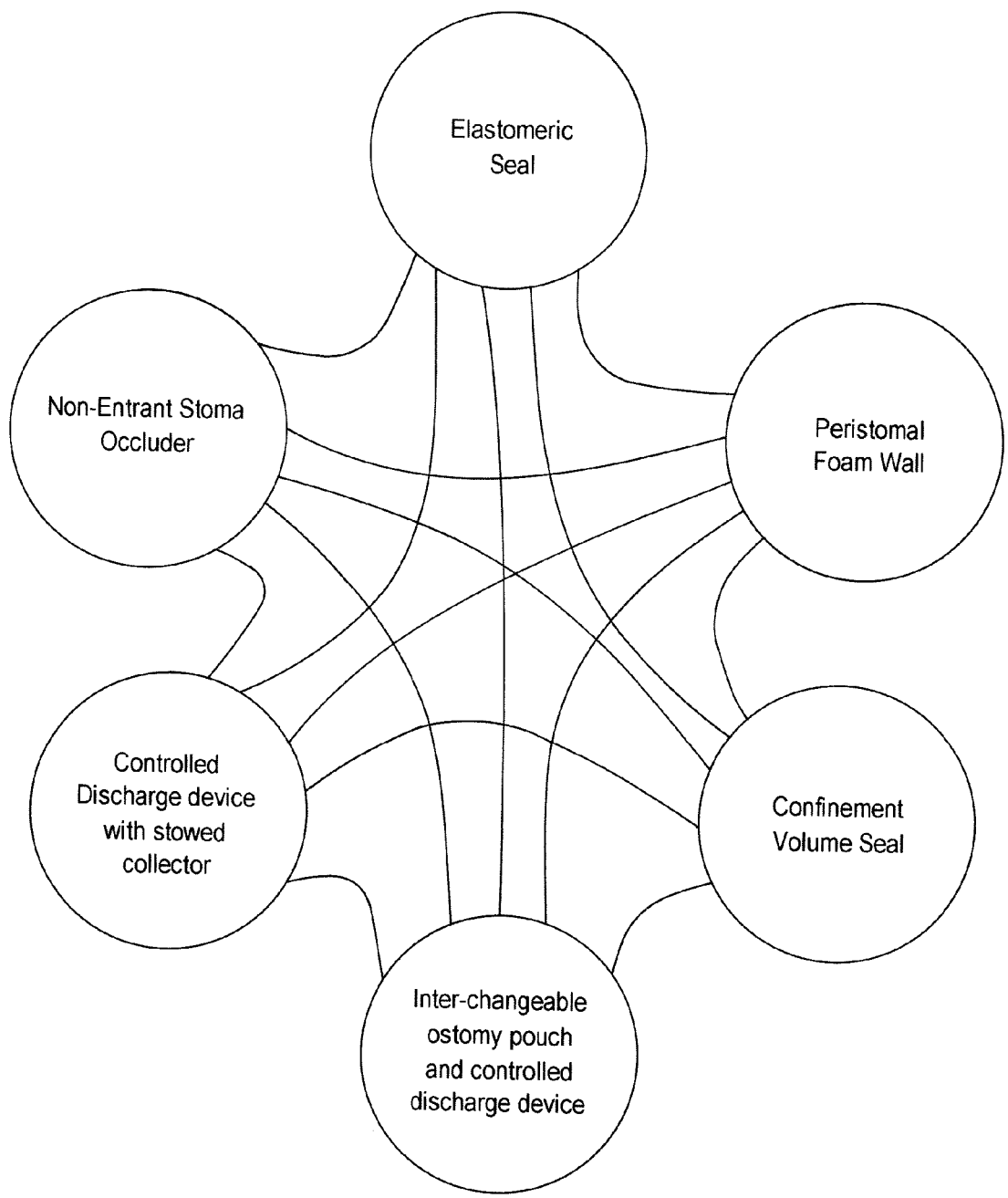
FIG. 1 is a combination diagram depicting selected combinable features of the invention, and as illustrated further in the preferred embodiments.

Embodiments 1 to 8 illustrate preferred configurations of an ostomy appliance comprising a faceplate employing a foam sealing gasket. The faceplate may be a mounting device for a waste collection pouch and/or a controlled discharge device. The faceplate may be part of a one-piece appliance or part of a multiple-piece appliance (e.g., comprising multiple, separable parts). Embodiments 9 to 22 illustrate preferred configurations of a controlled ostomy discharge device. The discharge devices may include any of the faceplate configurations of embodiments 1 to 8.

The cross-section drawings are partial views along a radius to a centerline (CL) through the stoma and stomal aperture of the appliance. The same reference numerals are used to denote equivalent features in the different embodiments, where appropriate.

Embodiment 1

Figure 2:
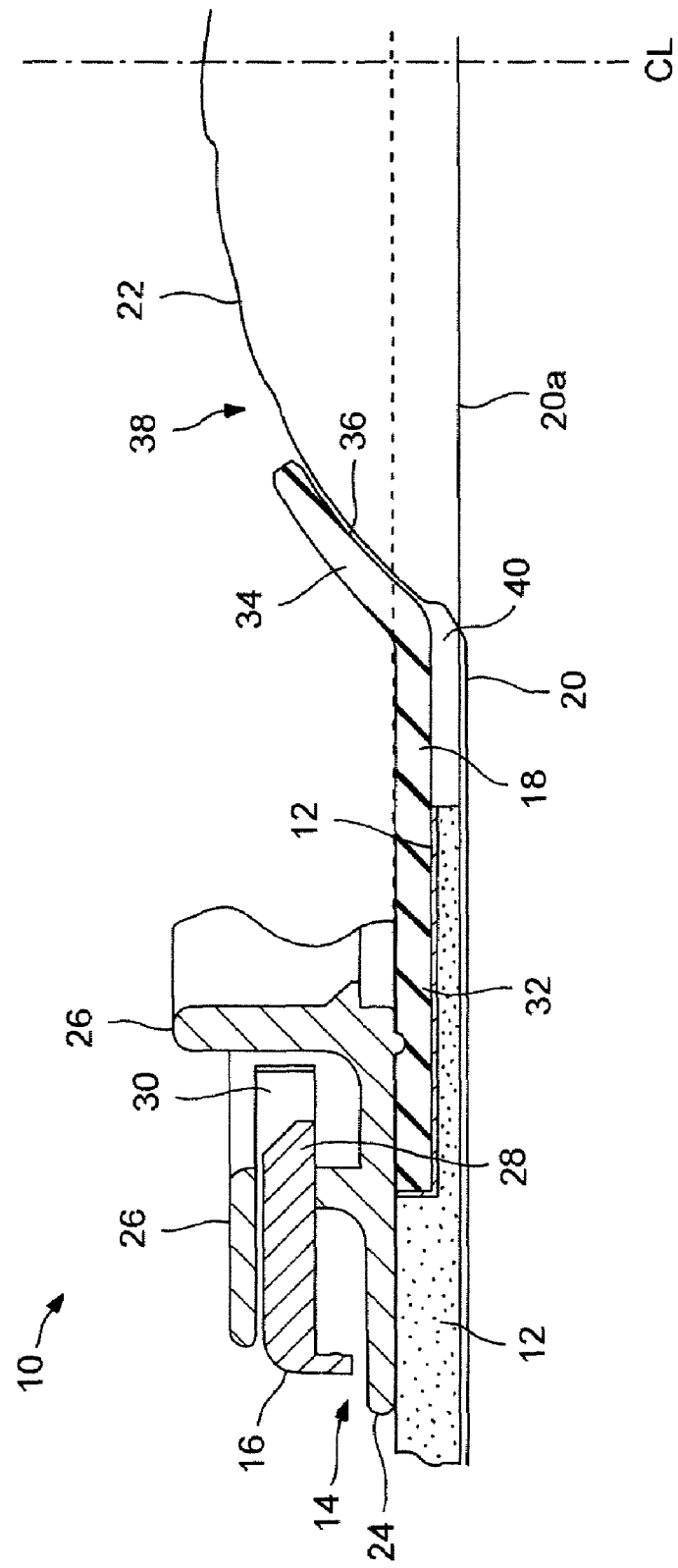
FIG. 2 is a schematic cross-section through part of a first embodiment of ostomy faceplate shown on the body.

Referring to FIG. 2, an ostomy faceplate 10 may generally comprise an adhesive member (or wafer) 12 for securing an ostomy appliance to the skin 20 around a stoma 22. The adhesive member 12 may be of closed loop (for example, circular) shape, and comprise a skin-friendly medical grade adhesive, for example, hydrocolloid based adhesive. The adhesive surface of the adhesive member 12 may initially be covered by a protective release sheet (not shown) that is peeled from the adhesive member 12 prior to use.

In the present embodiment, the appliance is of a two-piece type including a coupling for releasably securing the appliance to the faceplate 10. However, the same principles may be applied to a one-piece device without any form of releasably coupling to the faceplate. In the present embodiment, the releasable coupling comprises one or more plastics moldings 14, 16 for forming a mechanical interlock with a complementary coupling member (not shown) on the appliance. If the appliance comprises a collection pouch, then the complementary coupling member may be mounted on the collection pouch. If the appliance comprises a cap, then the complementary coupling member may be mounted on the cap. A first of the plastics moldings 14 may be of closed loop shape, and may generally comprise a flange 24 from which upstand one or more walls 26 for guiding engagement with the complementary coupling member (not shown). The second plastics molding 16 may generally comprise a split locking ring carried on the first plastics molding 14. The split locking ring may comprise a plurality of locking tabs 28 projecting through apertures 30 in one of the walls 26. The configuration of these exemplary plastics moldings 14 and 16, and their manner of operation to form a mechanical interlock with the complementary coupling member, are described in more detail in EP-A-0737456 (the contents are which are incorporated by reference). However, it will be appreciated that the invention is not limited to the type of coupling, and other mechanical or adhesive couplings may be used. Alternatively, the coupling may be omitted for a one-piece appliance.

The faceplate 10 further comprises a stoma sealing member 18 for sealing around the periphery of the stoma 22. The sealing member 18 may be of closed loop shape, and may generally take the form of a thin gasket comprising a support portion 32 and a stoma engaging portion 34. The support portion 32 may be radially outside, and integral with, the stoma engaging portion 34. In this embodiment, the support portion 32 may be generally planar, and may be received in a recess formed in the adhesive member 12, so as to be sandwiched between the adhesive member 12 and one of the plastics moldings 14. The support portion 32 may be secured in position by any suitable means, for example, by welding or by adhesive.

The stoma engaging portion 34 may be configured to overlap the stoma 22 for sealing against the stoma 22. The stoma engaging portion 34 may have a stoma contacting surface 36 of a generally closed loop, concave configuration, surrounding an opening 38. The concave configuration may be generally curved in an axial direction (e.g., flared or dished), or generally straight in an axial direction (e.g., frusto conical). The concave configuration enables the stoma contacting surface 36 to at least partly cup the surface of the stoma 22. Such a concave or cupped contact can provide a relatively large sealing area, especially in contrast to a convex sealing member that arcs away from the stoma surface.

The stoma engaging portion 34 may be profiled to have the concave configuration as its natural shape, or it may be deformable to the concave configuration when the appliance (or more particularly the sealing member 18) is fitted around the stoma. For example, the stoma engaging portion 34 may have a natural flat configuration, and deform to the concave configuration in use.

The sealing member 18 may be generally elastomeric, and substantially non-moldable (e.g., the sealing member is not easily plastically reshapable in normal use). When the faceplate 10 is fitted to the skin 20 by pressing the faceplate 10 on to the skin 20, the stoma contacting surface 36 of the sealing member 18 may bear against the stoma 22, at least partly in an axial direction (e.g., at least partly generally perpendicular to the skin surface). The sealing member 18 may exert a sealing force on the stoma 22 resulting from one or both of: the at least partly axial pressure; and hoop stress in the sealing member 18 created by slight expansion of the opening 38 to accommodate the girth of the stoma 22 as the sealing member 18 is pressed further down the tapered or rounded side of the stoma 22.

The sealing member 18 may, for example, be made of plastics foam or a low durometer elastomer such as Silicone or Urethane. These materials may provide excellent cushioning properties (e.g., for comfort), and excellent elastomeric conformity (e.g., to achieve a closely fitting seal). The sealing member 18 is preferably impermeable, and may be of closed cell foam, or of open cell foam having an impermeable surface or skin. The sealing member may also be of a composite structure with an impermeable bottom surface and an open cell upper element. Typically the sealing member 18 may be less than about 2 mm in thickness, for example, about 1 mm thick. However, sealing members greater than 1 or 2 mm in thickness may be used as well. Composite sealing members consisting of two or more materials may be 10 mm-13 mm or more in thickness.

A small clearance 40 is shown under the sealing member 18, resulting from the step shape of the adhesive member 12 for accommodating the sealing member 18. If desired, the clearance 40 may be filled, for example, by profiling the sealing member 18 to have a complementary step shape.

If desired, the ostomate may cut the stomal aperture 38 of the sealing member 18 to a size to match his or her stoma 22. This can provide a custom fit, and may be especially useful for irregular stoma shapes. Alternatively, the faceplate 10 may be supplied with a pre-sized sealing member 18.

The sealing member 18 seals the gap between the edge of the adhesive member 12 and the soma 22, to prevent body waste from contacting, and potentially leaking under, the adhesive member 12. The adhesive member 12 may erode if contacted by body waste, and the adhesive bond to the skin 20 may also be weakened or lose integrity. The resilience of the sealing member 18 can ensure a comfortable, yet snug fit around the stoma, and provide a reliable seal against waste egress. The concave configuration of the stoma contacting portion 34 provides a large sealing area.

Embodiment 2

Figure 3:
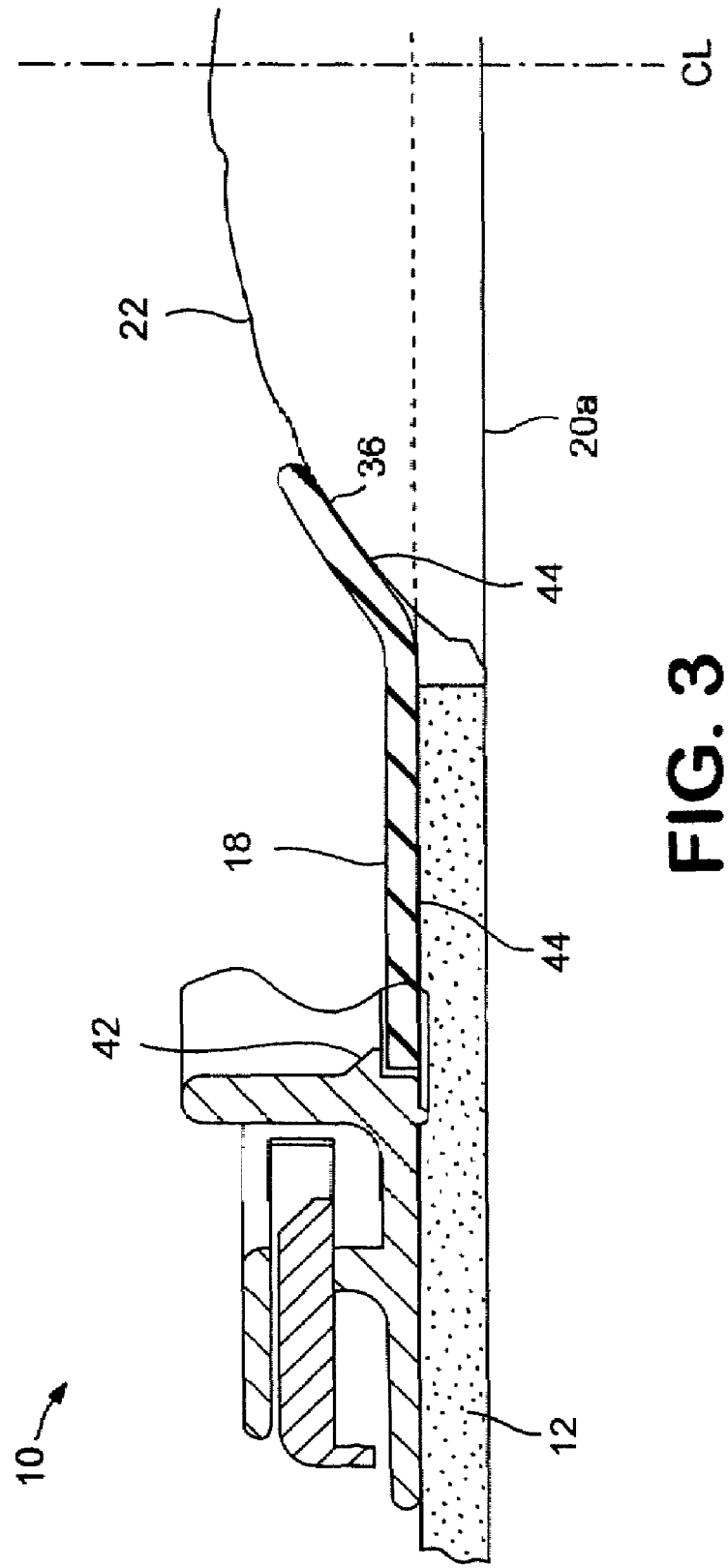
FIG. 3 is a schematic cross-section through part of a second embodiment of ostomy faceplate shown on the body.

Referring to FIG. 3, the faceplate 10 of the second embodiment is very similar to the first embodiment except for the positioning of the sealing member 18. In the second embodiment, the adhesive member 12 is not step-shaped. The sealing member 18 fits between the upper surface of the adhesive member 12 and an undercut lug 42. The lug 42 may have a continuous annular shape, or may comprise angularly spaced lug segments.

An adhesive, for example, a low tack adhesive 44 may be coated on the underside of the sealing member 18 to secure the sealing member to the adhesive member 12.

The adhesive 44 may also be coated over the stoma contacting surface 36 of the sealing member 18 to adhere the sealing member 18 to the stoma 22. An adhesive bond between the sealing member 18 and the stoma 22 may further improve the seal between the sealing member 18 and the stoma 22.

As illustrated in FIG. 3, the sealing member 18 of the second embodiment is located slightly further from the skin 20 than in first embodiment. In case this results in a smaller stoma contacting surface 36, the adhesive 44 may compensate for the reduced sealing area.

In this embodiment, the sealing member 18 may be fitted either during manufacture of the faceplate 10, or just prior to use by the ostomate. If desired, the stomal aperture of the adhesive member 12 and/or of the sealing member 18 may be trimmed to a size to match the stoma 22 just prior to securing the faceplate to the ostomate's skin 20. Additionally, or alternatively, the ostomate may have the facility to select a pre-sized sealing member 18 from a range of sealing member sizes.

Embodiment 3

Figure 4:
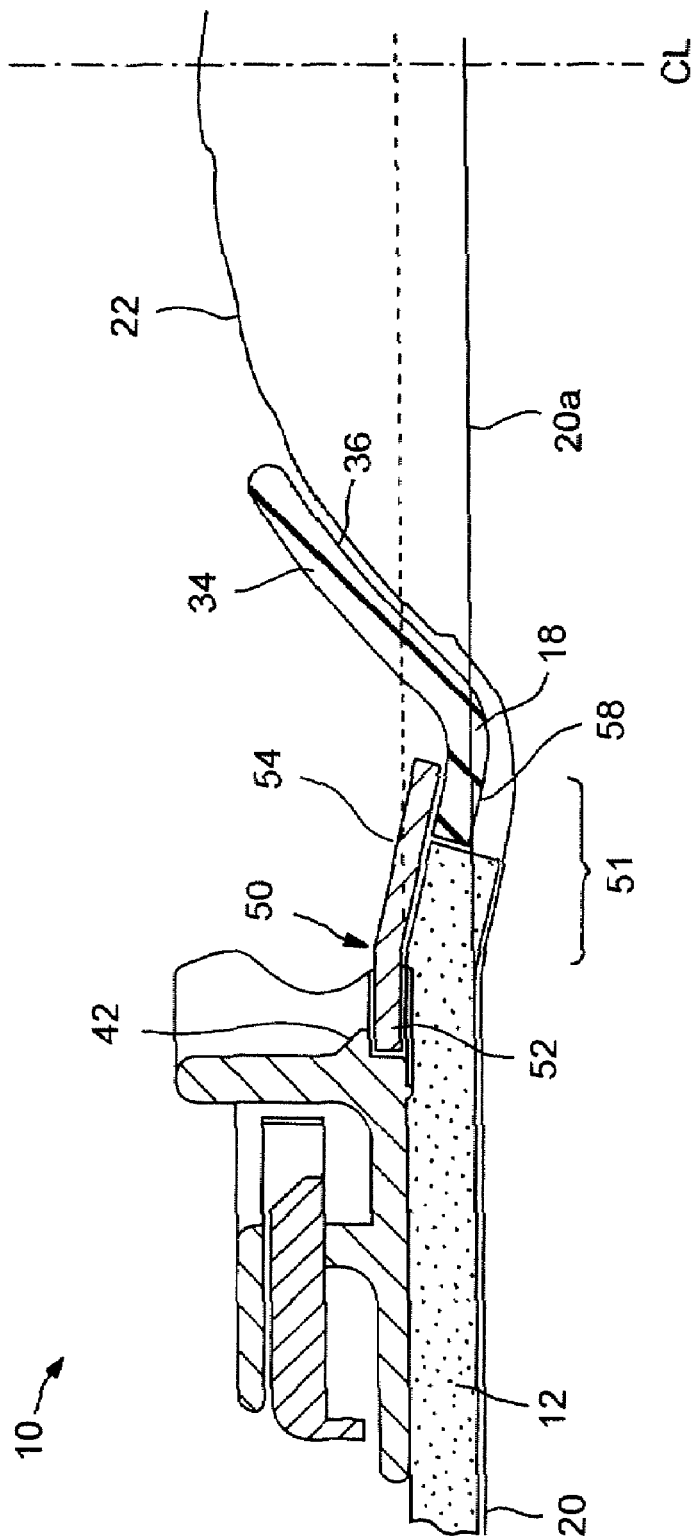
FIG. 4 is a schematic cross-section through part of a third embodiment of ostomy faceplate shown on the body.

Referring to FIG. 4, the faceplate 10 of the third embodiment is similar to that of the preceding embodiments, except that an additional shape defining member 50 is provided. The shape defining member 50 is shaped to define a convex bulge 51 to apply pressure to the skin 20 peristomally. The shape defining member 50 is preferably relatively stiff at least compared to the sealing member 18. The shape defining member 50 may be made of any suitable material, such as plastics (for example, polyethylene) or metal (for example, stainless steel). The shape defining member 50 may be substantially rigid, or resilient. In the present embodiment, the shape defining member 50 comprises a spring, in the form of a diaphragm spring having a support portion 52 engaged under the undercut lug 42 (described in the second embodiment), and a convex tapered (e.g., conical) portion 54. A spring is preferred to be able to adapt to different individual's stomas 22, and to provide a degree of cushioning for a comfortable fit.

The convex conical portion 54 bears partly on an inner peripheral portion 58 of the adhesive member 12, and partly on a peristomal portion 60 of the sealing member 18. The sealing member 18 may be fastened to the adhesive member 12 and/or to the shape defining member 50, or the sealing member 18 may be separate but held captive against the skin 20 by the shape defining member 18. Although not shown, the sealing member 18 may also extend further outwardly to be sandwiched between the adhesive member 12 and the shape defining member 50.

The shape defining member 50 of this embodiment does not bear directly against the stoma 22, and so the shape defining member 50 may be relatively stiff (at least compared to the sealing member 18). The shape defining member 50 serves to apply pressure to the skin 20 immediately adjacent to the stoma 22. This may offer one or more of the following advantages:

(a) An increase in the sealing area between the sealing member 18 and the stoma 22 and peristomal skin 20. For example, compared to the first and second embodiments, more of the surface area of the sealing member 18 may make sealing contact with the skin and stoma.

(b) The application of pressure peristomally results in a seal not only against the stoma 22, but also against the surrounding skin 20. The skin 20 is less sensitive than the stoma 22, and may tolerate a greater applied pressure without complications. Therefore, this arrangement may allow a greater sealing pressure to be used against the skin 20 than can be used against the stoma 22.

(c) The application of pressure peristomally tends to increase the protuberance of the stoma 22, at least with respect to the region of skin 20 to which pressure is applied. In the drawings, the line 20a represents the usual skin level. Increasing the degree of protuberance increases the surface area of the stoma 22 against which the stoma contacting surface 36 can seal, and also tends to urge the stoma 22 against the sealing member 18 more strongly.

The shape defining member 50 and/or the sealing member 18 may be fitted to the faceplate 10 during manufacture, or one or both may be fitted manually by the ostomate just prior to securing the faceplate 10 to the ostomate's skin. As in the previous embodiments, the sealing member 18 may be pre-sized, or the ostomate may trim the sealing member 18 to suit his or her stoma.

Embodiment 4

Figure 5:
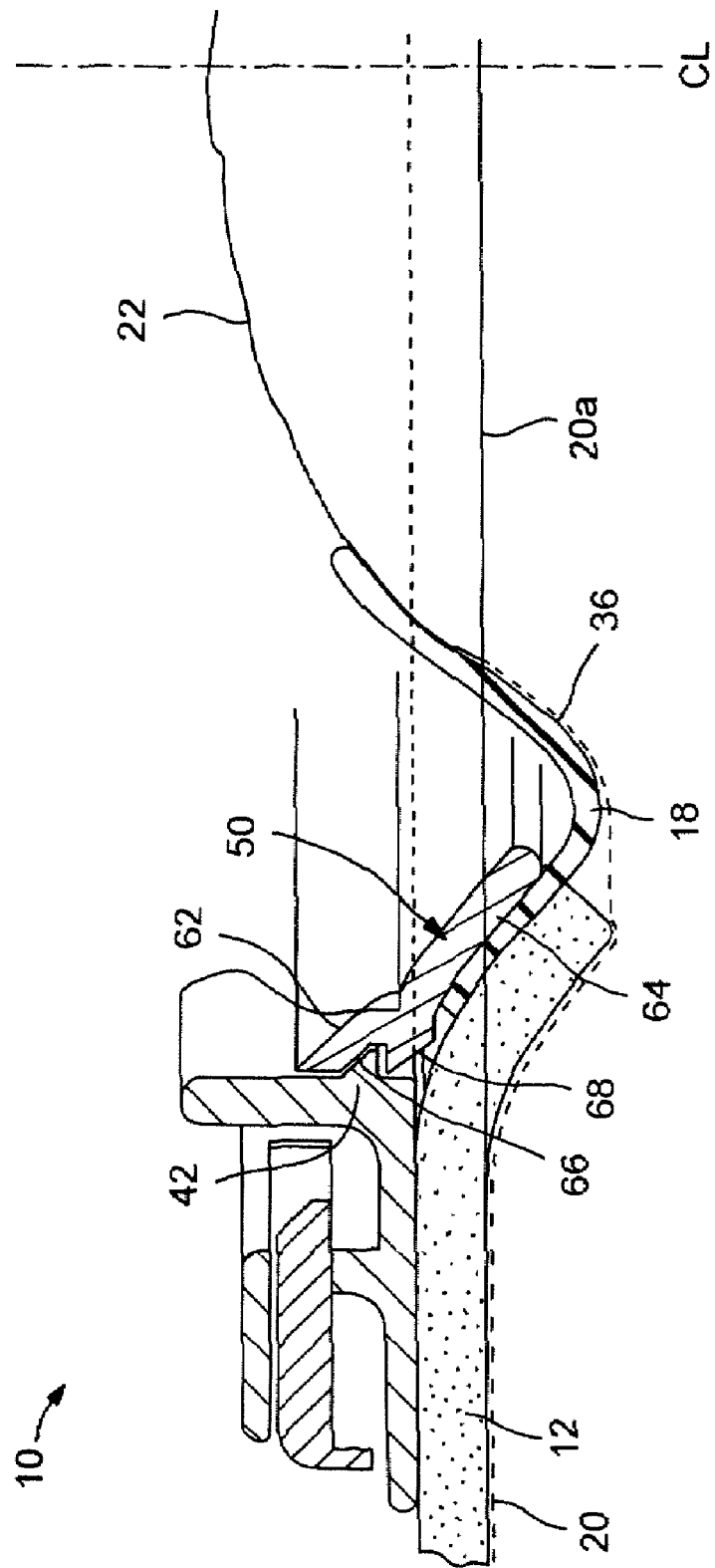
FIG. 5 is a schematic cross-section through part of a fourth embodiment of ostomy faceplate shown on the body.

Referring to FIG. 5, the fourth embodiment is similar to the third embodiment. The main differences relate to the configuration of the shape defining member 50. The shape defining member 50 comprises a molded plastics insert having a support portion 62 and a convex projection 64. The convex projection 64 may be substantially co-extensive with the adhesive member 12. The support portion 62 comprises a latch profile 66 for interlocking engagement with the lug 42 of the faceplate 10. The latch profile 66 includes a tapered lead-in surface 68 to enable the shape defining member 50 to be snapped into position.

The sealing member 18 overlaps, and is sandwiched between, the adhesive member 12 and the convex projection 64 to retain the sealing member 18 in position. The shape defining member 50 functions in the same manner as described in the third embodiment, to apply pressure to the peristomal skin 20 surrounding the stoma 22.

As in the third embodiment, the shape defining member 50 and/or the sealing member 18 may be fitted to the faceplate 10 during manufacture, or one or both may be fitted manually by the ostomate just prior to securing the faceplate 10 to the ostomate's skin. As in the previous embodiments, the sealing member 18 may be presized, or the ostomate may trim the sealing member 18 to suit his or her stoma. The adhesive member 12 may also be cut to size, if desired.

Embodiment 5

Figure 6:
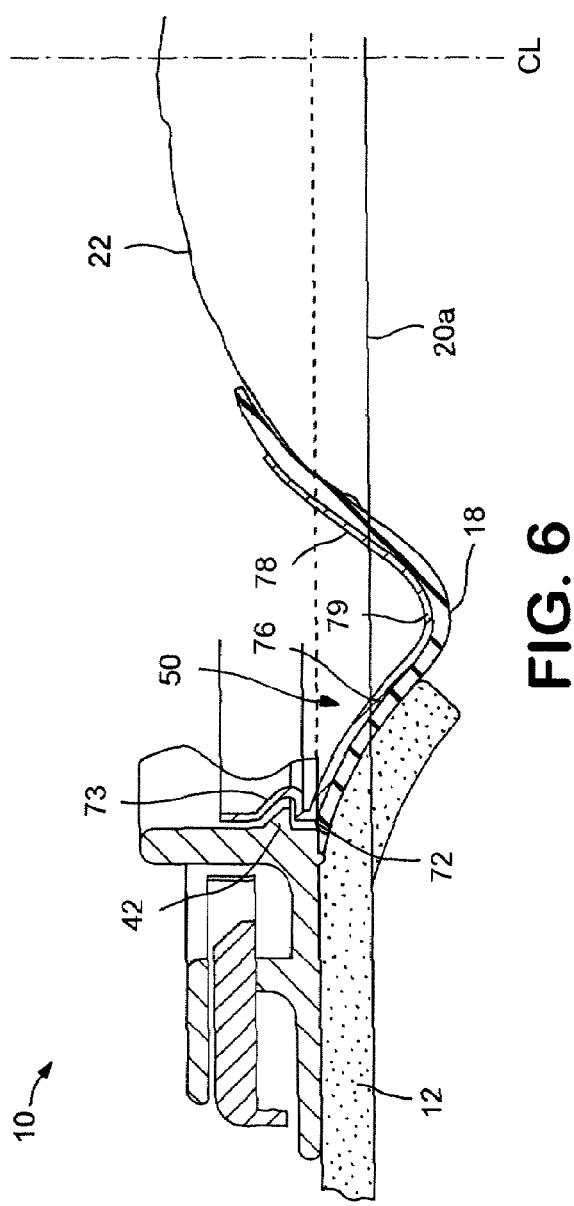
FIG. 6 is a schematic cross-section through part of a fifth embodiment of ostomy faceplate shown on the body.
Figure 7:
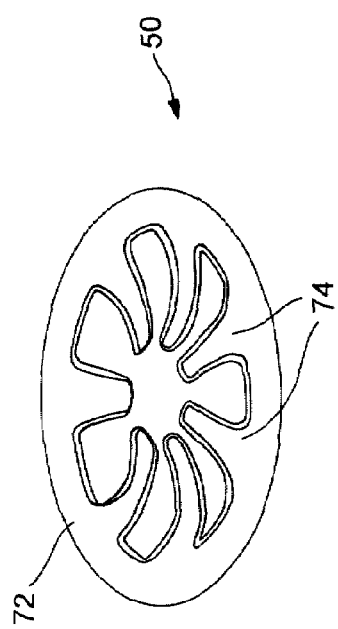
FIG. 7 is a schematic perspective view of a shape defining member of FIG. 6, shown in isolation.

Referring to FIGS. 6 and 7, the fifth embodiment is similar to the third and fourth embodiments. The main differences relate to the configuration of the shape defining member 50. In the third and fourth embodiments, the shape defining member 50 did not overlie the stoma 22, and did not apply pressure directly to the stoma 22. In the fifth embodiment, the shape defining member 50 is configured to apply pressure additionally to the stoma 22.

In this embodiment, it is preferred that the shape defining member 50 be at least partly resilient, to allow the sealing member 18 to conform to the shape of the stoma 22. The shape defining member 50 preferably comprises a rim portion 72 from which project a plurality of inwardly directed spring fingers 74. In the present example, seven fingers 74 are provided substantially equally angularly spaced from each other. However, in other embodiments, the number and placement of the fingers may be varied as desired.

Each spring finger 74 may be substantially V-shaped to provide a first convex portion 76 (similar to the convex portion 54 of the third embodiment), and a second return portion 78. The return portion 78 may be shaped to approximately match the concave shape of the stoma engaging portion 34 of the sealing member 18, to press the stoma engaging portion 34 against the stoma 22. The apex 79 of the V-shape of the spring finger 74 may be slightly rounded, for reasons of comfort. Although a V-shape is illustrated in FIG. 5, the spring fingers 74 may have any suitable convex or bulged shape to provide pressure against the peristomal skin 20, and additional part-axial and/or part-lateral pressure against the stoma 22.

In this embodiment, the spring fingers 74 can flex independently of one another, to adapt to the shape and size of the individual's stoma 22. For example, flexing of one spring finger 74 does not affect flexing of other spring fingers 74. This can allow the shape defining 50 member to urge the sealing member 18 tightly against the stoma surface, while still allowing a high degree of conformity to suit different stoma shapes and sizes.

The shape defining member 50 may be held in position by the lug 42 of the faceplate 10. The spring member 50 may further comprise a circumferential latch profile 73 with a complementary shape to the lug 42. The latch profile 73 may also provide additional strength for reinforcing the rim portion 72. Alternatively, if the latch profile 73 is omitted, then the rim portion 72 may locate under the lug 42 (as in the third embodiment).

As in the third embodiment, the shape defining member may be made of any suitable material, such as plastics or metal (for example, stainless steel).

In a similar manner to the fourth embodiment, the sealing member 18 may overlap the adhesive member 12 to be sandwiched between the adhesive member 12 and the shape defining member 50. In an alternative form, the sealing member 18 may be dimensioned to butt the inner peripheral edge of the adhesive member 12, as in the third embodiment.

Also, as in the third embodiment, the shape defining member 50 and/or the sealing member 18 may be fitted to the faceplate 10 during manufacture, or one or both may be fitted manually by the ostomate just prior to securing the faceplate 10 to the ostomate's skin. As in the previous embodiments, the sealing member 18 may be presized, or the ostomate may trim the sealing member 18 to suit his or her stoma.

Embodiment 6

Figure 8:
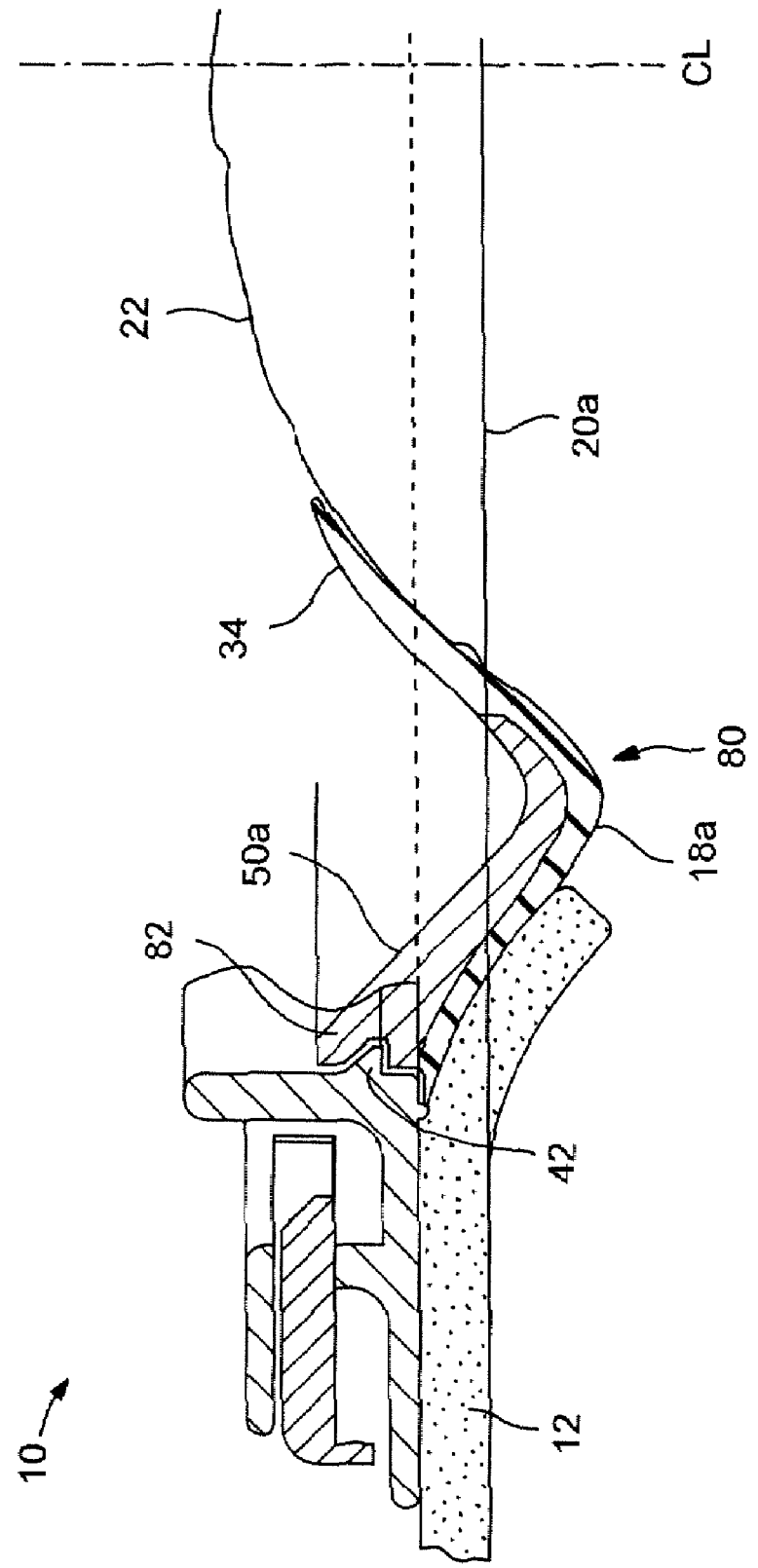
FIG. 8 is a schematic cross-section through part of a sixth embodiment of ostomy faceplate shown on the body.

Referring to FIG. 8, the sixth embodiment is similar to the fifth embodiment, except that the sealing member 18 and the shape defining member 50 are integrally formed as a unitary member 80, referred to herein as the unitary shape/sealing member 80. The unitary shape/sealing member 80 may be of plastics, and formed by integral molding, for example, multi-shot molding. The term "integral molding" may be used broadly to mean any molding process for integrally forming two different portions as a unitary member, and may rely, for example, on chemical bonding of different plastics materials, or mechanical keying between the two portions, or a combination of both.

In the present embodiment, the unitary shape/sealing member 80 comprises a first portion 18a of a first relatively soft elastomeric plastics, and one or more second portions 50a of a second relatively stiff plastics. The second portions 50a may be substantially rigid, or stiffly resilient. The first portion 18a may be equivalent to the sealing member 18 of the preceding embodiments. The one or more second portions 50a may serve to stiffen the first portion 18a in a similar manner to the shape defining member 50 of the third, fourth and fifth embodiments. Preferably, a plurality of second portions 50a are provided in the form of ribs. The ribs 50a may define a convex profile in a peristomal region of the first portion 18a. The ribs 50a may also be shaped to apply pressure, at least partly against the stoma 22. It is preferred that the first portion 18a extend further inward than the second portions 50a.

In the present embodiment, the second portions 50a may be independent (e.g., unconnected directly to one another). This can permit the unitary shape/sealing member 80 to flex in all directions, and allows the unitary shape/sealing member 80 to adapt to the shape and size of an individual's stoma 22.

The second portions 50a may be molded with a latch profile 82 for forming a mechanical interlock with the rib 42 of the faceplate 10, to hold the unitary shape/sealing member 80 in position. The unitary shape/sealing member 80 may be fitted to the faceplate 10 either during manufacture, or it may be fitted by the ostomate just prior to adhering the faceplate 10 to the skin 20. If desired, the ostomate may trim the inner periphery of the first portion 18a to suit his or her stoma size.

Embodiment 7

Figure 9:
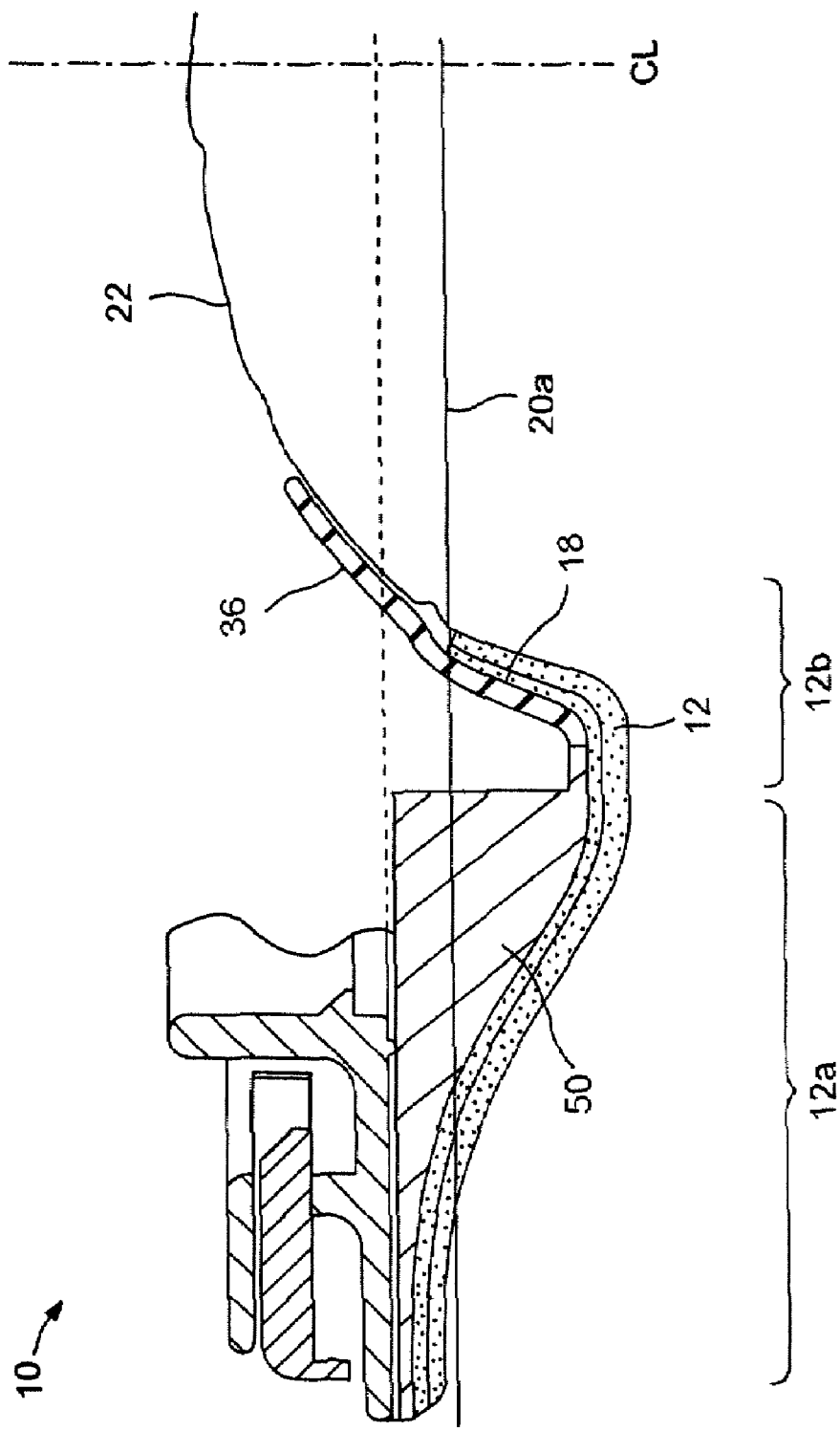
FIG. 9 is a schematic cross-section through part of a seventh embodiment of ostomy faceplate shown on the body.

Referring to FIG. 9, the seventh embodiment is similar to the third to sixth embodiments. The main differences relate to the configuration of the shape defining member 50 and the adhesive member 12. The adhesive member 12 may include a first zone 12a supported by the shape defining member 50 to have a well defined, bulged shape. The adhesive member 12 may include a second zone 12b unsupported by the shape defining member 50, so as to allow at least a degree of moldability. The second zone 12b may be shapeable by the ostomate to adapt the adhesive member 12 to suit the individual's stoma size and shape. In particular, the ostomate can shape the adhesive in the second zone 12b to form a custom fit around and/or against the stoma 22.

The sealing member 18 may overlap, and be secured to, the adhesive in the second zone 12b. For example, the sealing member 18 may be secured by an adhesive surface of the adhesive member 12, or the sealing member may be bonded or welded to the adhesive member 12. As in previous embodiments, the sealing member 18 may include an elastomeric concave configuration to cup the surface of the stoma 22. The adhesive attachment of the second zone of the adhesive to the stoma 22 provides may provide additional support for the elastomeric sealing member 18. The adhesive member 12 may be partly elastic to provide a degree of spring-back, such that the adhesive tends to elastically hug the stoma 22 and/or such elasticity may result from the elastomeric nature of the sealing member 18.

Embodiment 8

Figure 19:
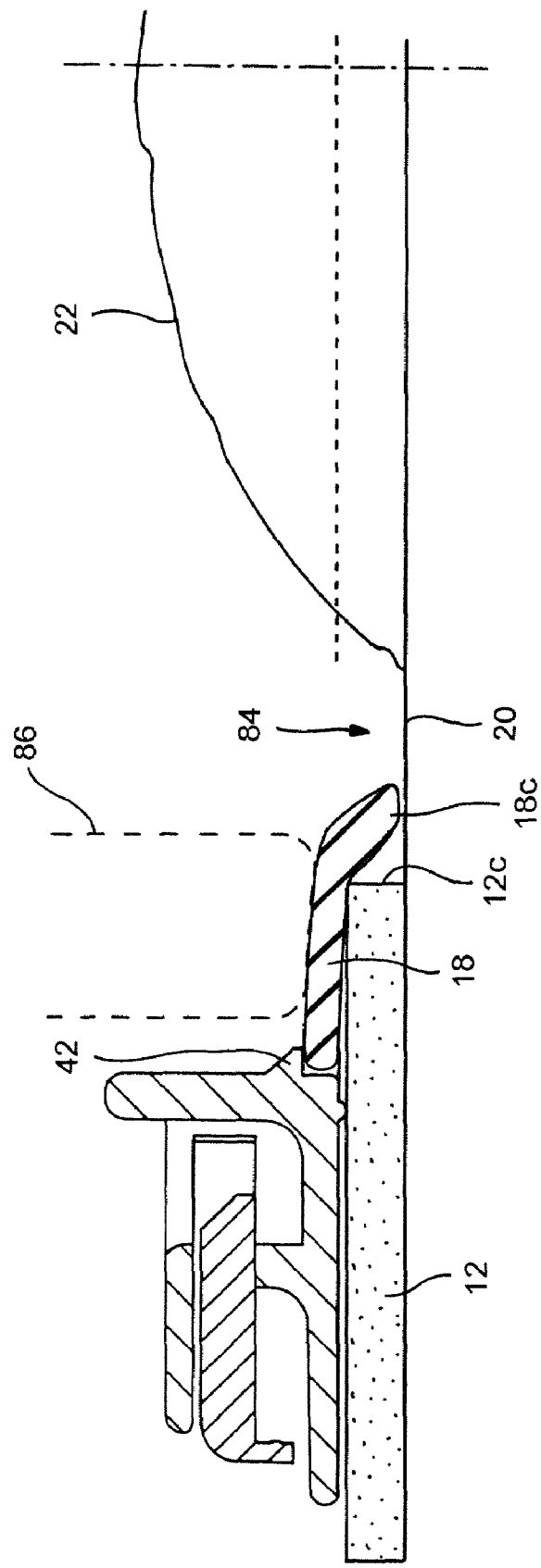
FIG. 19 is a schematic cross-section through part of an eighth embodiment of ostomy faceplate shown on the body.

Referring to FIG. 19, the eighth embodiment may be similar to the first and second embodiments. The main differences relate to the configuration of the sealing member 18. In the eighth embodiment, the seal member 18 is configured not to directly contact the stoma 22. Instead, the adhesive pad 12 may be cut-back slightly to leave a clearance 84 between an inner edge 12c of the adhesive pad 12 and the stoma 22. An inner edge portion 18c of the sealing member 18 may be configured to partly overlap the inner edge of the sealing member 18, and extend into the clearance 84. The sealing member 18 therefore protect the inner edge of the adhesive pad from exposure to stomal discharge and/or prevent (or at least obstruct) leakage of stomal discharge between the skin 20 and the adhesive pad 12. The sealing member 18 may be located by the undercut 42 and/or by pressure applied from another portion of the appliance in a direction towards the skin.

A pressure applying member (indicated in phantom at 86) may be arranged on the side (or face) of the sealing member facing away from the skin 20. The pressure applying member may comprise an inflatable device and/or a member of compressible foam material. The foam material may be of closed cell foam, or of open cell foam, depending on the permeability characteristics desired for solid, liquid and gas body waste. The pressure applying member 86 may apply pressure from another portion (not shown) of the ostomy appliance in a direction towards the skin when the other portion is attached to the faceplate 10. For example, the other portion may be a collection pouch and/or a controlled discharge device. The pressure applying member 86 may at least partly overlie the clearance 84 and/or the inner edge of the adhesive pad 12. In this embodiment, the pressure applying member 86 does not directly overlie the stoma 22. The pressure applying member 86 may be unitary with the sealing member 18 (as a composite member), or the pressure applying member 86 may be separate or separable from the sealing member 18.

The sealing member 150 and/or the adhesive pad 12 may be pre-sized, or one or both of these elements may be cut to a desired shape and/or size by the ostomate.

Although not illustrated explicitly in FIG. 19, a shape defining member 50/80 of one or more of the preceding embodiments may be used in the eighth embodiment, to further increase the sealing force exerted through the sealing member 18.

Embodiment 9

Figure 10:
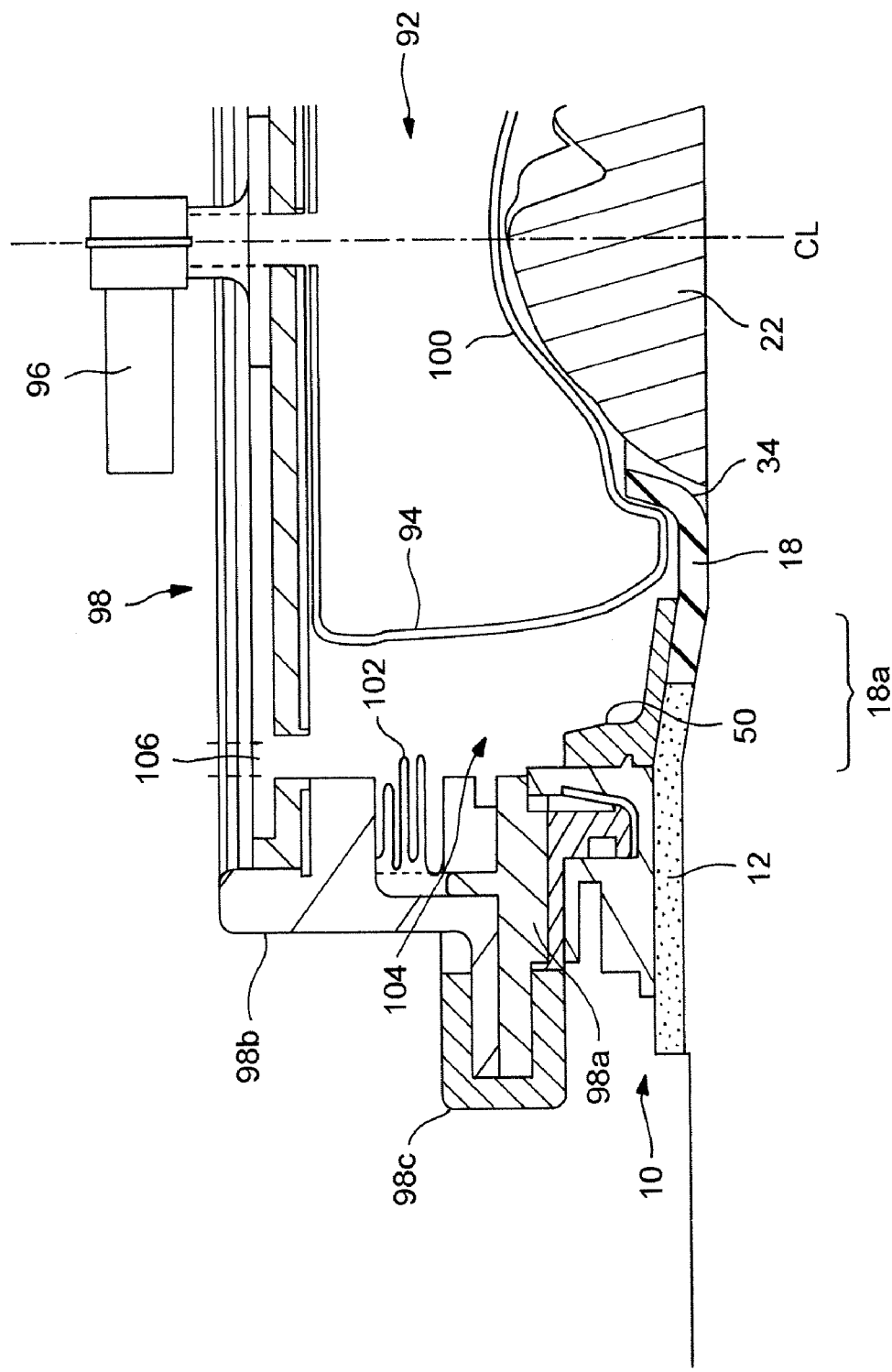
FIG. 10 is a schematic cross-section through part of a ninth embodiment of a controlled ostomy discharge device shown on the body.

Referring to FIG. 10, the ninth embodiment relates to a controlled discharge device 90 which may include the faceplate 10 and elastomeric sealing member 18 of any of the preceding embodiments. In FIG. 10, the sealing member 18 is depicted schematically to have a peristomal bulge 18*a*, and a stoma contacting surface, but it will be appreciated that the specific shape and configuration of the sealing member 18 and/or the shape defining member 50/80 (if provided), and the adhesive member 12, may vary, for example, as illustrated in the preceding embodiments.

The controlled discharge device may further comprise a non-entrant stoma occluder 92 in the form of an inflatable balloon 94. The balloon 94 may be inflated using any suitable inflation fluid, for example, a liquid (such as saline) or a gas (such as air). The inflation fluid may be supplied through an inflation port or conduit 96 from a pump (not shown). An inflation/deflation valve (not shown) may also be provided. The balloon 94 may be supported in a cap 98 secured permanently or releasably to the faceplate 10, for example, via the plastics moldings 14 and 16. The balloon 94 may be of an elastic material, or of a non-elastic material.

When the balloon 94 is inflated, a stoma occluding surface 100 of the balloon 94 may be urged against the stoma 22. The stoma occluding surface 100 may drape over the stoma 22, and also over the stoma engaging portion 34 of the elastomeric sealing member 18. The stoma occluding surface 100 may be profiled (e.g., pleated or constrained, or molded) to have a non-planar shape. For example, the stoma occluding surface may have a natural concave shape generally to complement the shape of the stoma 22. Alternatively, the stoma occluding surface 100 may have a natural planar shape which may crease and/or fold as the stoma occluding surface 100 is pressed against the projecting stoma 22, to adapt to the projecting shape.

A waste collector 102 may be incorporated into the appliance. The collector 102 may be collapsible, for example, as a bellows. The collector 102 may be in the form of a sleeve or tube that is attached to the cap 98 radially outside the stoma occluder 92. The cap 98 may consist of a lower coupling part 98*a* (first member) for coupling to the faceplate 10, and an upper cover part 98*b* (second member) for covering the lower part 98*a*. The upper and lower parts 98*a* and 98 may be releasably fastened, or fastenable, together. For example, a releasable fastening 98*c* may be used for fastening the upper and lower parts 98*a* and 98 together. The releasable fastening 98*c* may be refastenable after release, or it may be a one-time release device. The collector 102 may extend between the two cap parts 98*a* and 98*b*. The collector 102 may be collapsible into a stowed condition (illustrated in FIG. 10) when the lower and upper parts 98*a* and 98*b* of the cap 98 are secured together.

The collector 102 defines a collection volume 104 around the occluder 92. One or more flatus vents 106 may be provided in the cap 98 or in the wall of the collector 102 to allow flatus to vent from the collection volume 104. Each flatus vent 106 may include a deodorising filter (not shown). The deodorizing filter may be a conventional deodorizing filter commonly used in ostomy pouches.

In use, when it is desired to prevent, or at least obstruct, the discharge of waste from the stoma, the lower and upper parts 98*a* and 98*b* of the cap are fastened together, and the cap 98 is secured to the faceplate 10. The balloon 94 is inflated to occlude the stoma 22 (as depicted in FIG. 10). The pressure in the balloon 94 may generally be sufficient to obstruct egress of solid, semi-solid and liquid waste from the stoma 22. Flatus gas may have sufficient pressure to lift the stoma engaging surface 100 of the balloon 94 partly away from the stoma 22, and to create small, temporary channels under the stoma engaging surface 100 to allow the flatus to escape to the surrounding collection volume 104. From the collection volume 104, the flatus may vent to the surrounding atmosphere via the one or more flatus vents 106.

The elastomeric sealing member 18 provides a precautionary seal around the stoma 22 in case any solid, semi-solid or liquid waste should leak from the stoma 22 past the stoma occluder 92. Leakage of waste might occur due to a pressure drop inside the balloon 94, for example, should any of the inflation fluid leak or should the balloon volume increase to accommodate a change in distance between the balloon 94 and the stoma 22. Also, when the appliance 10 is worn for long periods of time, liquid or semi-solid waste may leak with the passing of flatus. In such a case, it may be important to prevent the body waste from contacting the adhesive member 12. Body waste may erode the adhesive member 12 (leading to possible adhesive failure), or the body waste may leak out between the adhesive member 12 and the skin.

The environment within a controlled discharge device may be completely different from that in a normal ostomy pouch. For example, in an ostomy pouch, waste is permitted to flow substantially unobstructed from the stoma into the pouch. Therefore, a conventional stoma seal for an ostomy pouch does not have to withstand considerable pressure of waste acting on the seal. In contrast, in the controlled discharge device as illustrated in FIG. 10, any body waste leaking under the balloon 94 is confined to the collapsed collection volume 104 defined by the collapsed collector 102. The body waste may therefore be under considerable pressure. The elastomeric sealing member 18 can provide a strong seal around the stoma 22 to prevent any such leaked waste matter from reaching the adhesive member 12. Should the waste matter be under pressure, then the shape of the elastomeric sealing member 18 may utilize the pressure to increase the sealing force against, or around, the stoma 22. For example, pressure acting on the surface of the sealing member 18 facing away from the stoma 22 and/or the peristomal skin may increase the sealing force on, or around, the stoma 22, to provide a stronger seal. Therefore, the elastomeric sealing member 18 may enable a more durable seal to be obtained than conventional stoma seals (e.g., typically used for ostomy pouches) that may not provide sufficient seal strength for an externally acting controlled discharge device.

When it is desired to allow waste discharge from the stoma 22, the balloon 94 may optionally be deflated, and the upper cap part 98b may be released from lower cap part 98a. This extends (or at least permits extension of) the collector 102, to expand the collection volume 104. Since the stoma occluder 92 does not now occlude the stoma 22, body waste is able to be discharged freely from the stoma 22 into the collector 102. The collector 102 therefore provides for hygienic discharge of waste after the stoma 22 has been occluded for a period of time. Once the discharge has been completed, the lower cap part 98a may be released from the faceplate 10 for disposal, and a fresh cap assembly 98 fitted to the faceplate 10.

Although the present embodiment enables the faceplate 10 to remain in position for use with replaceable cap assemblies 98, other embodiments may be configured for disposal of the faceplate 10 with the collector 102 and the cap assembly 98 (in a similar manner to a one-piece ostomy pouch). For example, the lower cap part 98a may be permanently secured to the faceplate 10, or the lower cap part 98a may be omitted (and the collector 102 sealed directly to the upper cap part 98a and the faceplate 10).

Embodiment 10

Figure 11:
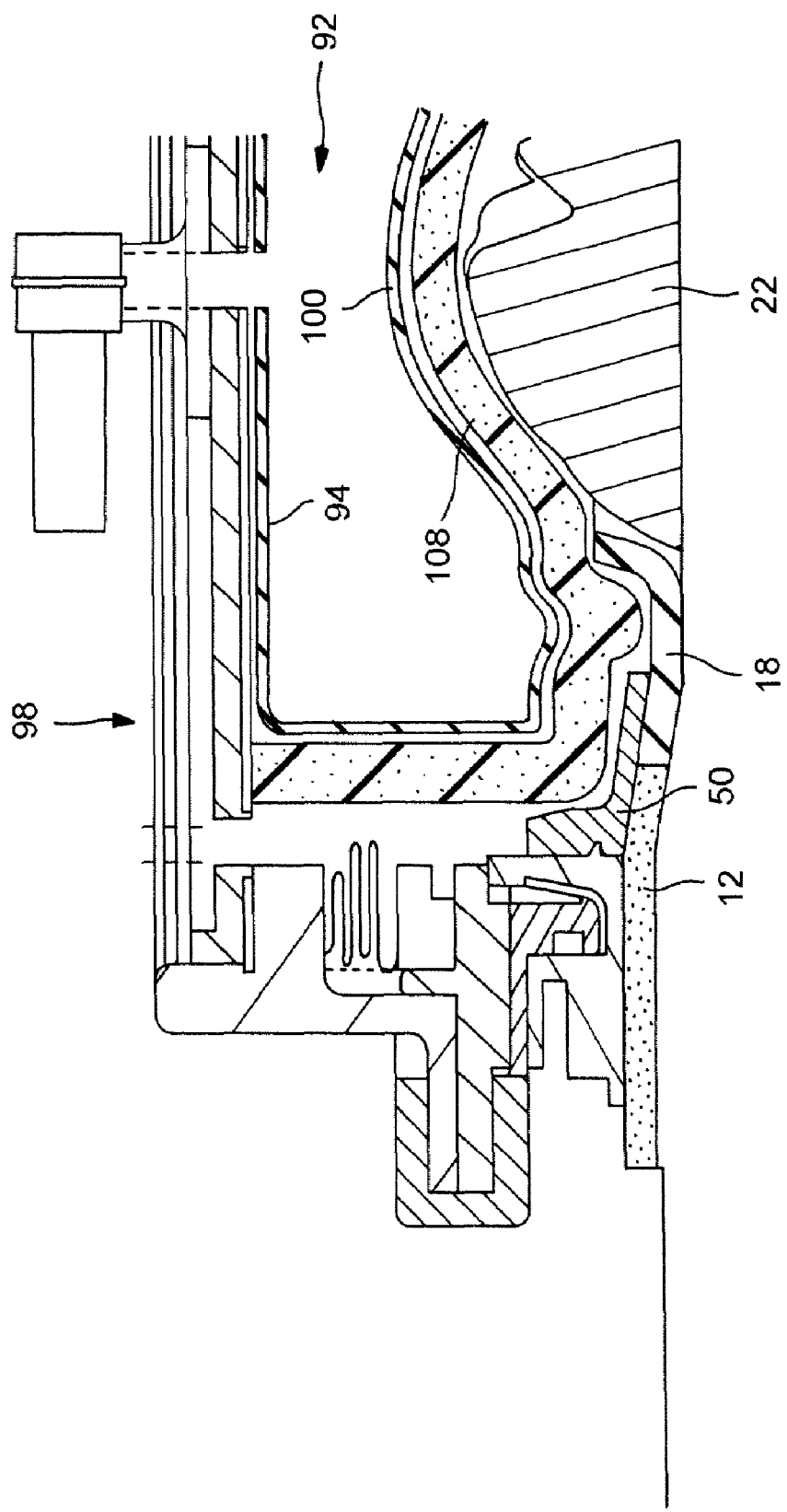
FIG. 11 is a schematic cross-section through part of a tenth embodiment of a controlled ostomy discharge device shown on the body.

Referring to FIG. 11, the tenth embodiment is very similar to the ninth embodiment. The main difference is the provision of a layer 108 of compressible foam extending at least in front of the stoma occluding surface 100 of the balloon 94. The foam layer 108 may provide one or more of the following functions:

(a) The foam layer 108 may provide a soft comfort cushion against the stoma 22;
(b) The foam wall 108 may be of, or comprise, open cell foam. Open cell foam may be permeable to gas, but may obstruct solid passage, and may soak-up liquid entering the foam material. Liquid may separate from gas by virtue of surface tension of the liquid in the foam cells. The foam wall 108 may therefore act as a separator to separate solid, liquid and gas waste products, and provide an obstruction to solids and to liquids, while permitting the passage of gas.

Such a separation function may be advantageous to avoid physical lifting of the stoma occluding surface 100 of the balloon to pass flatus. The foam wall 108 may be profiled to generate its own sealing force against the stoma 22 and/or the sealing force may be the provided by the internal pressure within the balloon 94.

If the foam layer 108 is intended to be permeable to gas, the foam layer may be left unskinned, or it may be provided with a gas permeable skin (not shown). If the foam layer is intended to be impermeable to gas, then a non-permeable skin (not shown) may be used and/or the foam wall 108 may be of closed cell foam.

Embodiment 11

Figure 12:
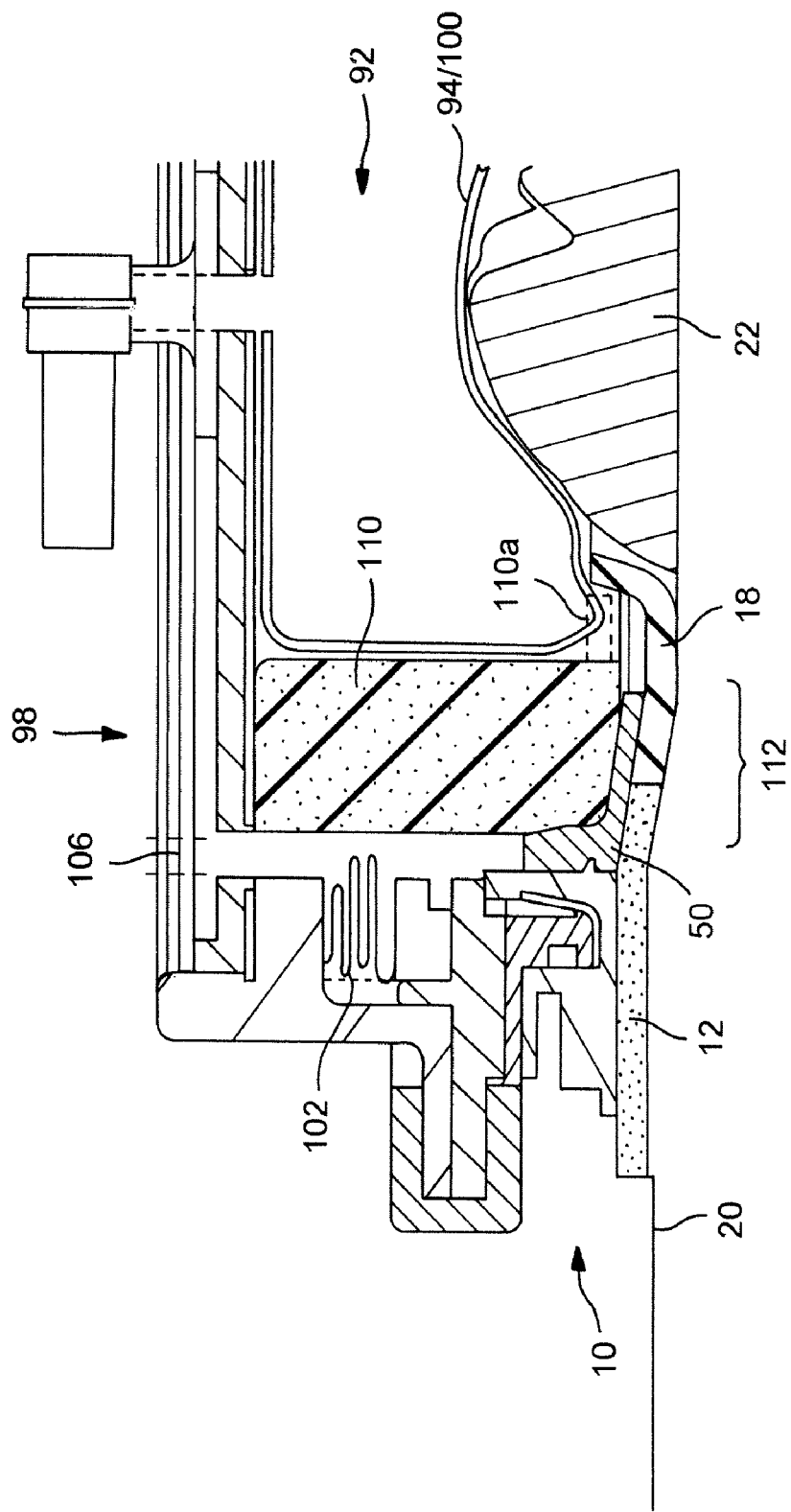
FIG. 12 is a schematic cross-section through part of an eleventh embodiment of a controlled ostomy discharge device shown on the body.

Referring to FIG. 12, the eleventh embodiment is very similar to the ninth embodiment. The main difference is the provision of a foam wall 110 around the stoma 22. The foam wall 110 may have a generally closed loop shape, for example, annular. In the present embodiment, the foam wall 110 may provide one or more of the following effects:

(a) The foam wall 110 may be resiliently compressible, and may be dimensioned to have a natural height that is greater than the distance between the cap 98 and the faceplate 10 when coupled together. The foam wall 110 may be compressed axially when the cap 98 is secured to the faceplate 10, thereby applying a restoring force directly or indirectly to a region 112 of the faceplate 10 contacting the foam wall 110.

The region 112 may include, or be, any of: a portion of the adhesive member 12; a portion of the elastomeric sealing member 18; a portion of the shape defining member 50 (if present); a portion of the unitary shape/sealing member 80 (if present). The foam wall 110 can therefore provide an additional force in a direction to increase the sealing force of the sealing member 18 against the stoma 22 and/or against the peristomal skin 20.

(b) The foam wall 110 may be of, or comprise, open cell foam. Open cell foam may be permeable to gas, but may obstruct solid passage, and may soak-up liquid entering the foam material. Liquid may separate from gas by virtue of surface tension of the liquid in the foam cells. The foam wall 110 may therefore act as a separator to separate solid, liquid and gas waste products.

(c) The foam wall may act as at least part of a confinement volume seal for confining solid and liquid stomal discharge, and establishing a seal between the separable portions of the cap 98.

As can be seen in FIG. 12, the foam wall 110 may be arranged to be radially inside any flatus vents 106 in the cap 98 and/or in the wall of the collector 102. The foam wall 110 can provide a degree of protection against leakage of liquid or semi-liquid waste through the flatus vents 106 (and also prevent soiling of any deodorizing filters, if present). The foam wall 110 may be secured to one or both of the faceplate 10 and the cap 98. The foam wall 110 may be secured permanently or releasably.

As illustrated in phantom at 110a in FIG. 12, the foam wall 110 may be provided with an inwardly extending lip 110a. The lip 110a may permit transfer of the axial sealing force from the internal pressure of the balloon 94, to increase the axial force exerted by the foam wall 110 in the faceplate region 112.

If desired, the collector 102 may be omitted. Instead, the foam wall 110 may provide a reliable barrier to solid, semi-solid and liquid waste leakage. Any accumulated body waste 98 may need to be cleaned if or when the cap 98 is released from the faceplate 10.

Embodiment 12

Figure 13:
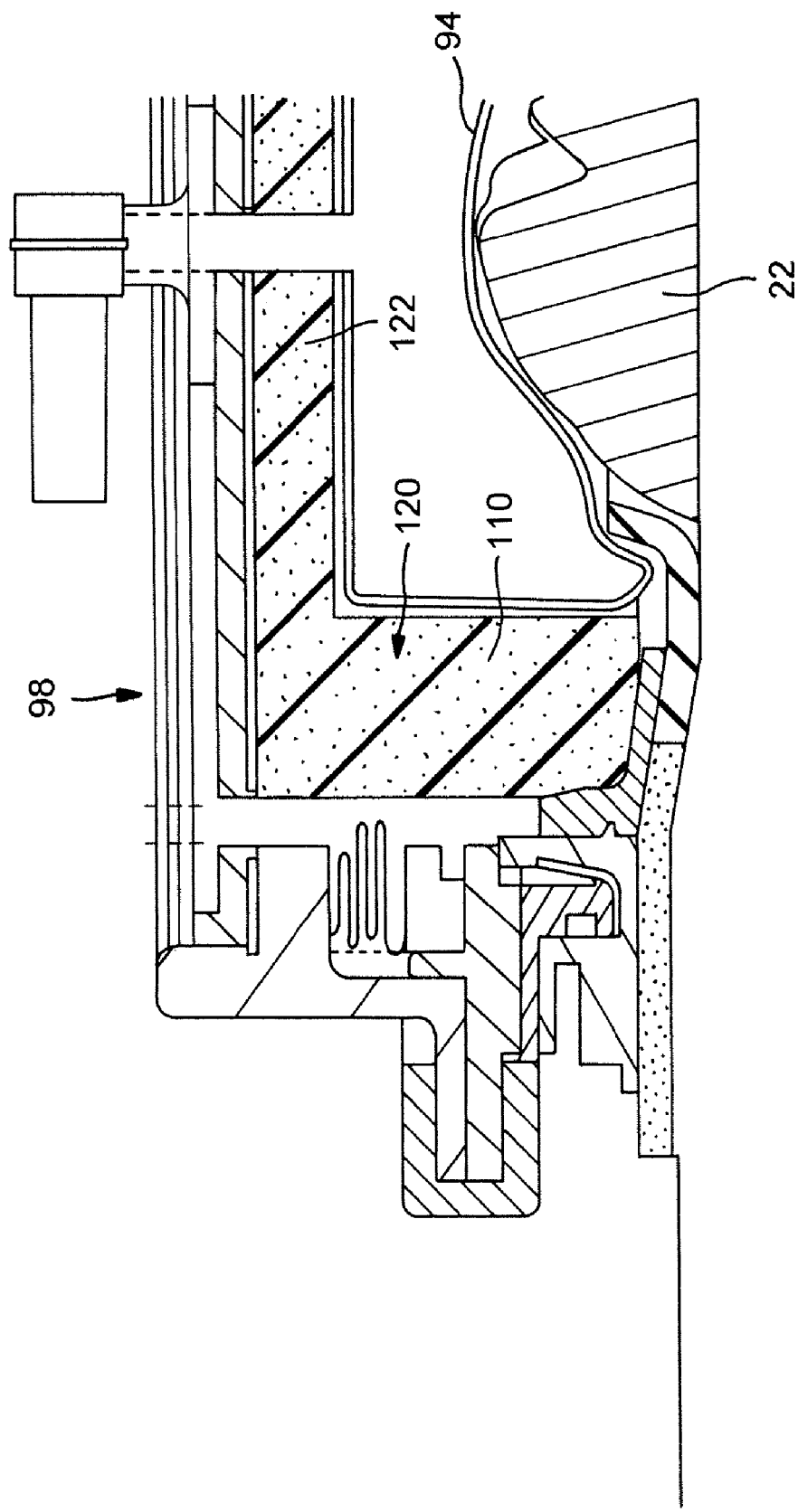
FIG. 13 is a schematic cross-section through part of a twelfth embodiment of a controlled ostomy discharge device shown on the body.

Referring to FIG. 13, the twelfth embodiment is very similar to the eleventh embodiment. The main difference is that the foam wall 110 is part of a foam member 120 that includes a portion 122 extending behind the inflatable balloon 94. The portion 122 may act as a compressible spring between the cap 98 and the balloon 94 to urge the balloon 94 against the stoma 22. Urging the balloon 94 against the stoma 22 may be advantageous in reducing the volume of the balloon 94, and also reducing the effects of a drop in pressure of the inflation fluid inside the balloon. The spring effect of the foam portion 122 may also assist in accommodating changes of distance between the stoma 22 and the cap 98.

Embodiment 13

Figure 14:
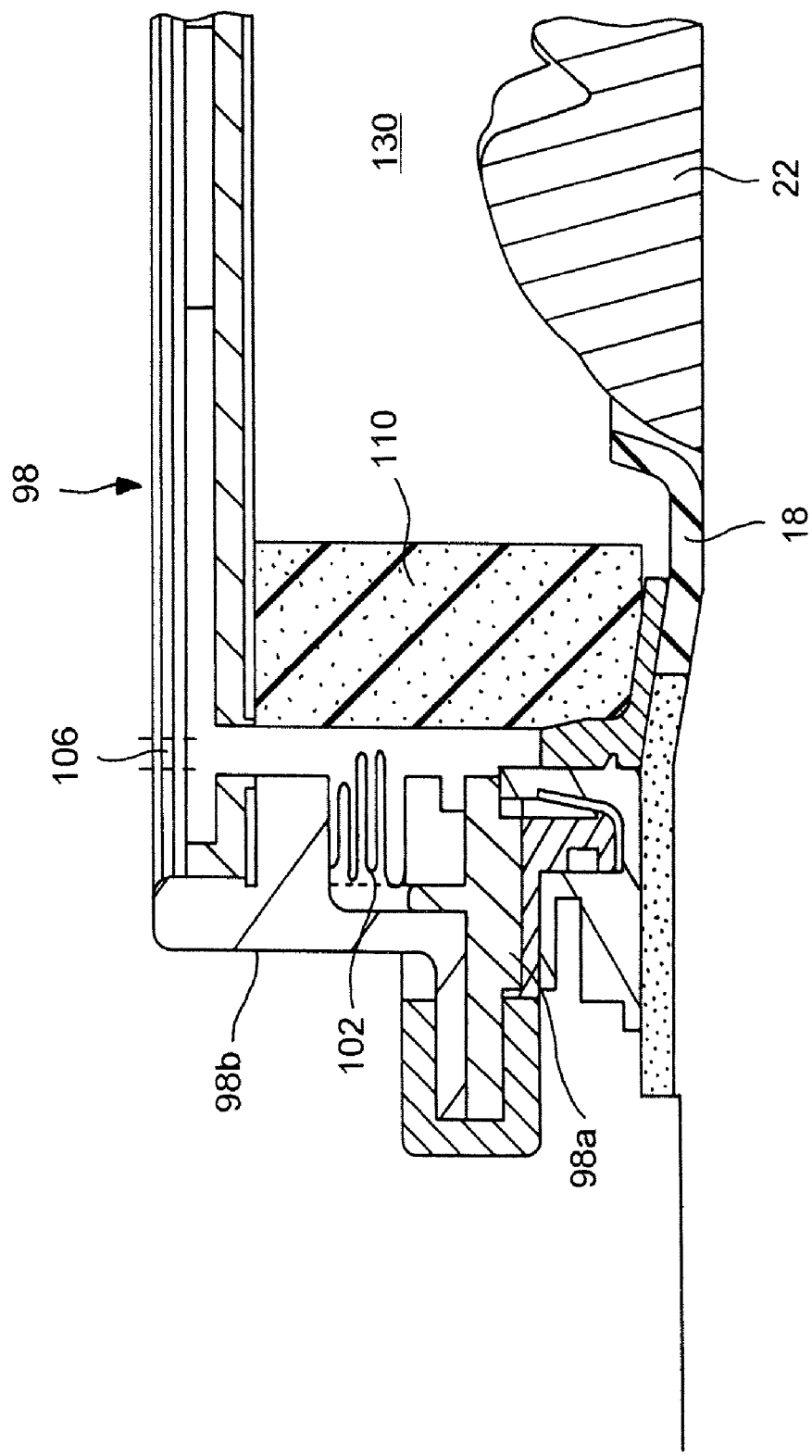
FIG. 14 is a schematic cross-section through part of a thirteenth embodiment of a controlled ostomy discharge device shown on the body.

Referring to FIG. 14, the thirteenth embodiment is similar to the eleventh embodiment, except that the inflatable balloon 94 (occluder 92) is omitted. Instead, the foam wall 110 surrounds the stoma 22 (as described in the tenth embodiment) and defines a confinement region 130 for body waste exiting the stoma 22. As before, the foam wall 110 acts as at least part of a confinement volume seal for sealing between separable portions of the cap 98. In this embodiment, the stoma 22 is not directly occluded, but waste matter is confined to the small confinement region 130. The foam wall 110 may act as a separator to confine solid waste, and also liquid or semi-solid waste. As explained previously, liquid waste may partly soak into the foam wall 110, but generally does not pass through the foam material. Gas may pass through the foam wall 110 to vent through the flatus vents 106.

The foam wall may provide one of more of functions (a)-(c) described in the eleventh embodiment. Function (a) may be advantageous to enhance the sealing properties of the elastomeric sealing member 18, because sealing member 18 is directly exposed to body waste that is permitted to exude from the stoma 22 until the confinement region 130 becomes filled.

Function (b) may be advantageous because the occluder 92 of the eleventh embodiment is no longer present to confine solid and liquid waste matter within the stoma 22. The foam wall 110 may therefore provide a primary separation function to allow flatus to escape.

Function (c) may be advantageous because the occluder 92 of the eleventh embodiment is no longer present to confine solid and liquid waste within the stoma 22. The foam wall 110 may therefore provide a primary seal function to define the confinement volume, for example, relative to the separable parts of the cap 98.

When it is desired to allow waste discharge, the upper part 98*b* of the cap 98 is released from the lower cap part 98*a*. This extends (or at least permits extension of) the collector 102, to expand the collection volume 104. Body waste accumulated in the confinement region 130 is able to be discharged freely into the collector 102. The collector 102 therefore provides for hygienic discharge of waste after the appliance has been used to obstruct stomal discharge for a period of time. Once discharge has been completed, the cap assembly 98 and the collector 102 may be separated from the faceplate 10 for disposal, and replaced using a fresh cap assembly 98 and collector 102.

Embodiment 14

Figure 15:
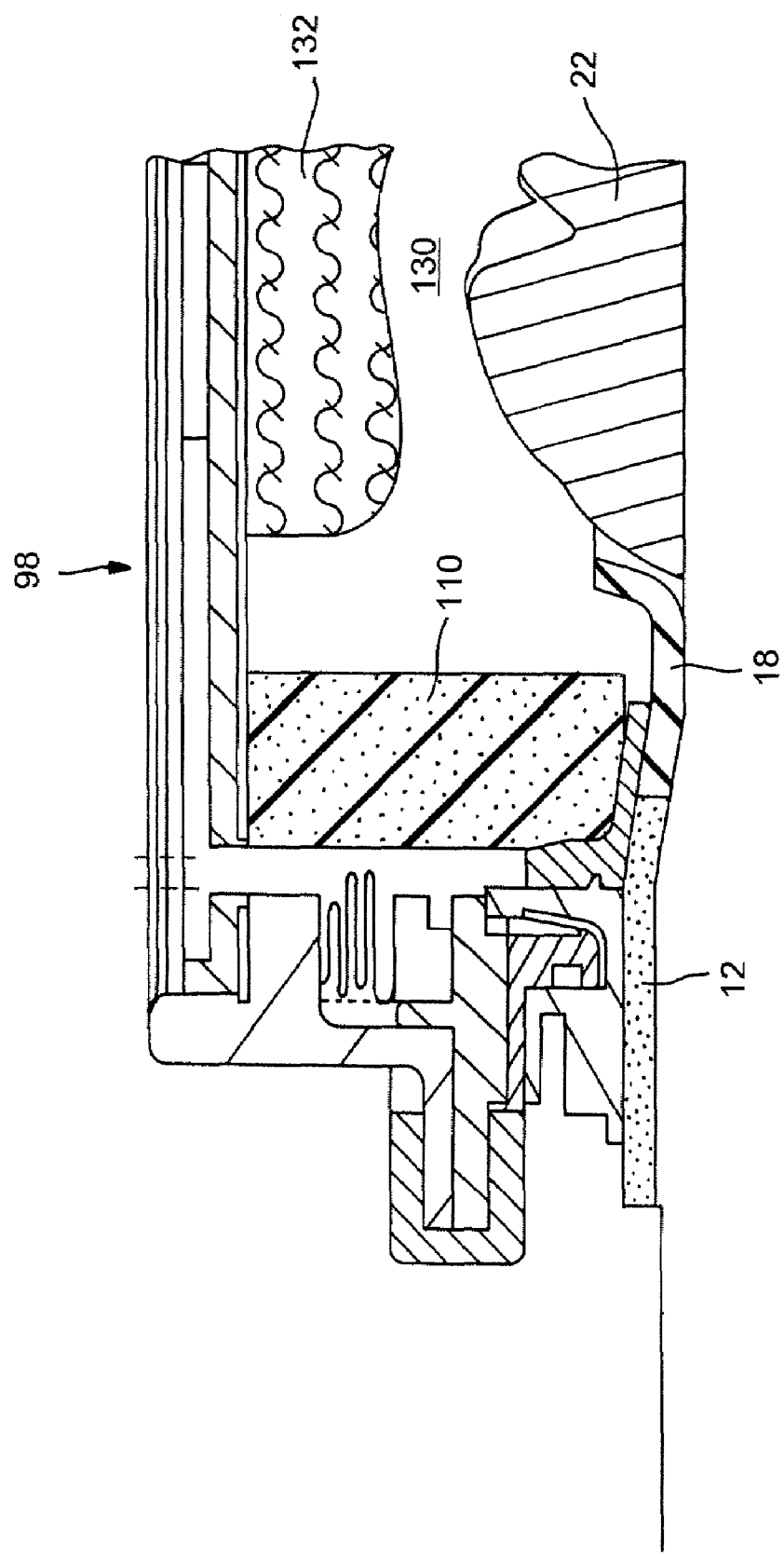
FIG. 15 is a schematic cross-section through part of a fourteenth embodiment of a controlled ostomy discharge device shown on the body.

Referring to FIG. 15, the fourteenth embodiment is very similar to the thirteenth embodiment. The main difference is that an absorbent member 132 of or containing absorbent material is provided in the confinement region 130 defined by the foam wall 110. The absorbent material may, for example, be a superabsorbent. A suitable super absorbent is, for example, an alkali metal methyl methacrylate. The absorbent member 132 may be secured to the interior surface of the cap 98, for example, by a heat seal or by adhesive.

The absorbent member 132 may serve one or both of:
  (a) To absorb liquid or semi-solid waste matter discharged from the stoma 22 into the confinement region 130. Absorption of such waste may extend the duration for which the foam wall 110 may function before the foam wall 110 may become overly-saturated.
  (b) To at least partly fill the confinement region 130, in order to reduce a "head" or volume of solid body waste that may accumulate outside the stoma 22 in the confinement region 130. In some cases, it may be desirable to reduce such an external accumulation of solid waste, to increase the ostomate's perception of cleanliness.

If the absorbent member 132 is or contains superabsorbent, then the absorbent member 132 may tend to expand as it absorbs liquid. Such expansion can increase the degree to which the absorbent member 132 fills or occupies the confinement region 130.

Embodiment 15

Figure 16:
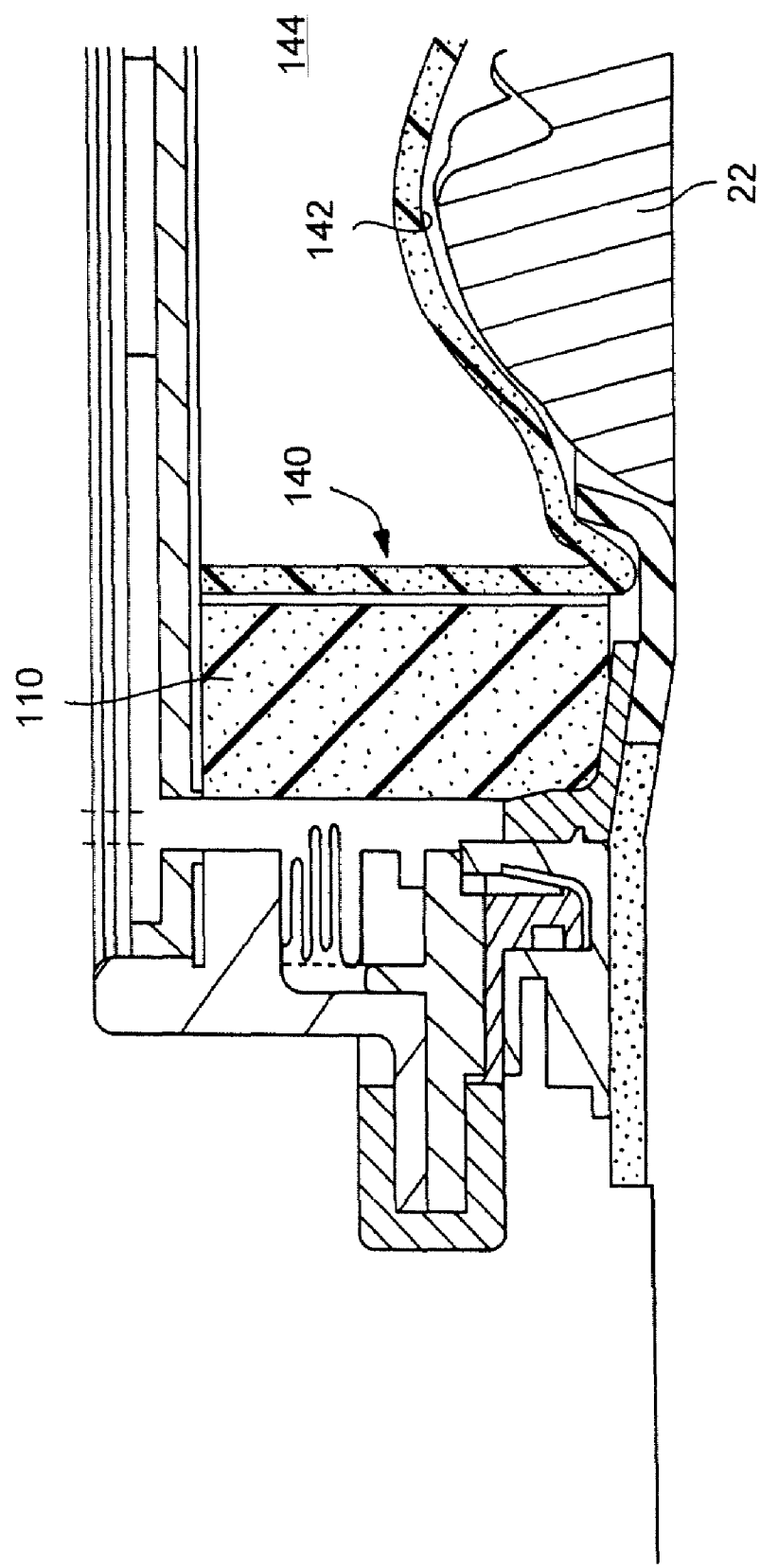
FIG. 16 is a schematic cross-section through part of a fifteenth embodiment of a controlled ostomy discharge device shown on the body.

Referring to FIG. 16, the fifteenth embodiment is similar to the tenth embodiment, except that the inflatable balloon 94 is replaced by a foam stoma occluder 140. The foam stoma occluder 140 may be a separate member from the foam wall 110 (as illustrated in FIG. 16), or the foam stoma occluder 140 and the foam wall 110 may be integrally formed as a unitary member.

The foam stoma occluder 140 is preferably resilient, and may be of open cell foam and/or of closed cell foam. The foam stoma occluder 140 may have a generally planar stoma occluding surface 142, or it may be profiled with a non-planar stoma occluding surface 142. For example, the foam stoma occluder 140 may be profiled to have a concave shape generally to match the shape of the stoma 22.

The foam stoma occluder 142 may be generally hollow, and define an open region 144 behind the stoma occluding surface 142.

The foam stoma occluder 140 may perform one or both of the following functions:
  (a) The foam stoma occluder 140 may at least partly prevent the open region 144 from filling with solid body waste from the stoma 22. Preventing the free accumulation of solid body waste may give the ostomate more of an impression of cleanliness;
  (b) The foam stoma occluder may function at least partly as a separator to separate and allow the passage of flatus gas, while at least partly obstructing the passage of solid, semi-solid and liquid body waste. The separation principles are similar to those discussed in feature (b) of the tenth and eleventh embodiments.

Depending on the properties desired for the foam stoma occluder 140, the foam may be open-cell foam or closed-cell foam. One or both of the surfaces of the foam stoma occluder 140 may be skinned (not shown), and each skin may be permeable or non-permeable.

Embodiment 16

Figure 17:
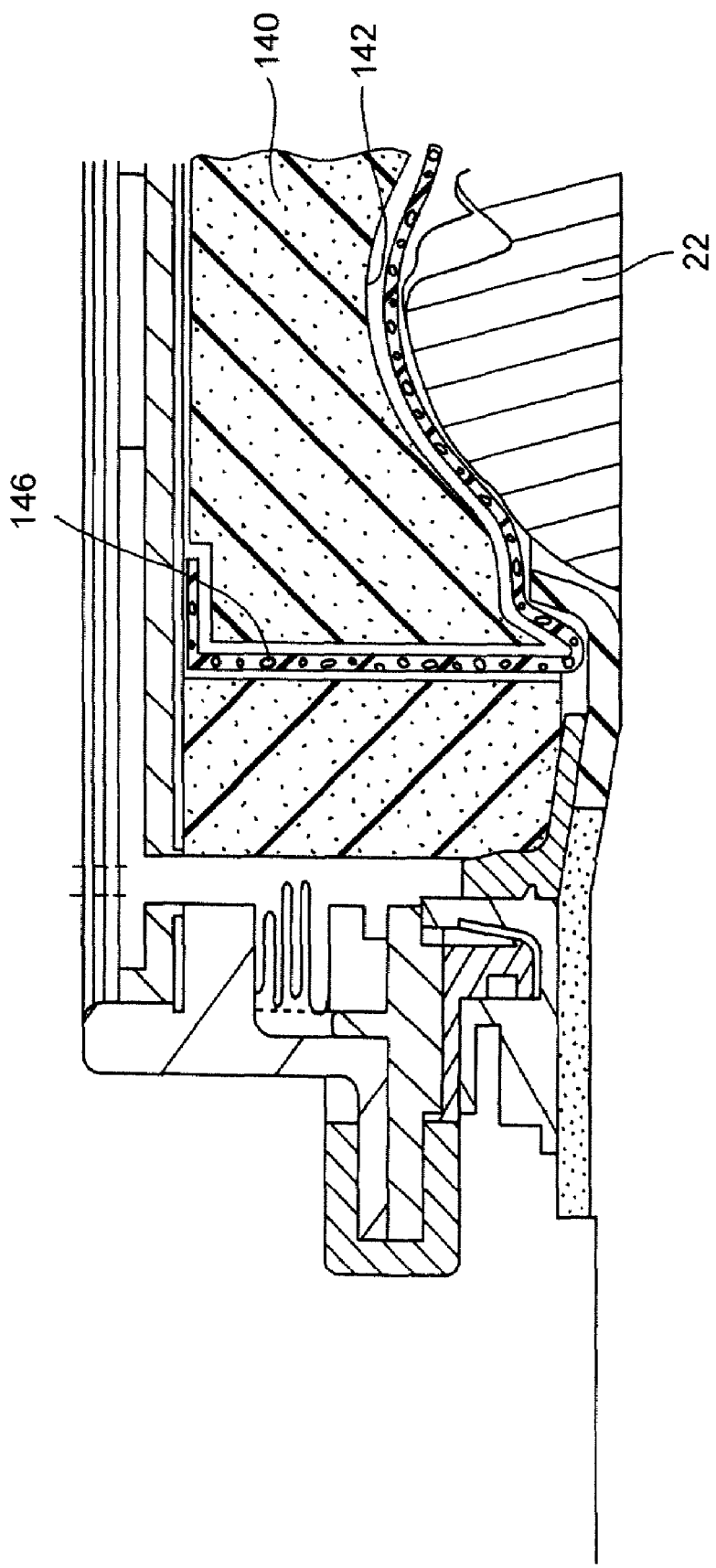
FIG. 17 is a schematic cross-section through part of a sixteenth embodiment of a controlled ostomy discharge device shown on the body.

Referring to FIG. 17, the sixteenth embodiment is similar to the fifteenth embodiment. The main difference lies in the configuration of the foam stoma occluder 140. In the present embodiment, the foam stoma occluder 140 is a solid member without any open region 144 of the fifteenth embodiment.

The foam stoma occluder 140 is preferably resilient to conform to the shape of the stoma 22, and to form a close fit thereagainst.

A flexible membrane or surround 146 may surround at least the stoma occluding surface 142 of the foam stoma occluder 140. As in the previous embodiment, depending on the desired properties, the flexible surround 146 and/or the foam stoma occluder 140 may be configured to be generally gas permeable or generally impermeable.

Embodiment 17

Figure 18:
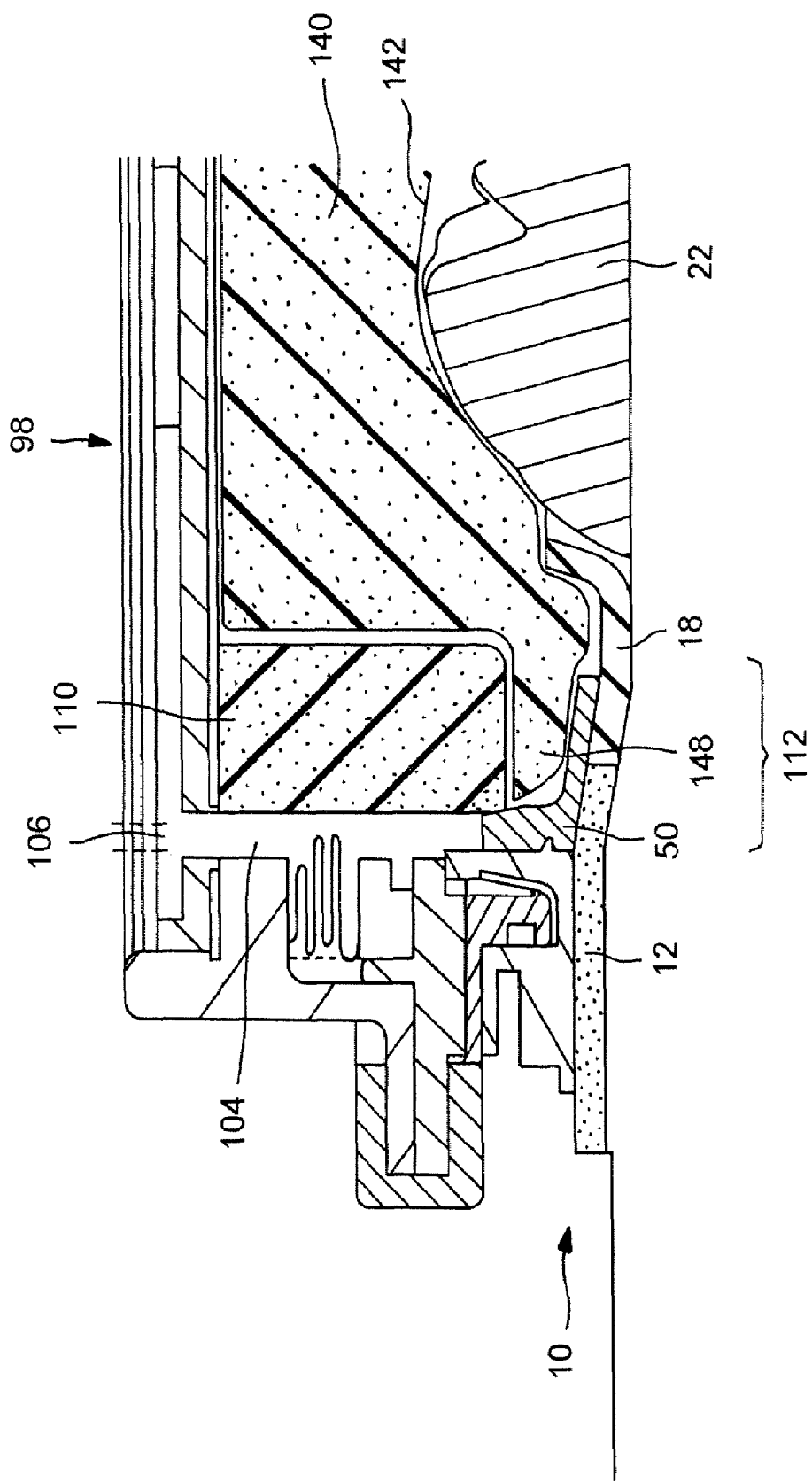
FIG. 18 is a schematic cross-section through part of a seventeenth embodiment of a controlled ostomy discharge device shown on the body.

Referring to FIG. 18, the seventeenth embodiment is very similar to the fifteenth and sixteenth embodiments. The main difference is the configuration of the foam stoma occluder 140. In the present embodiment, a foam stoma occluder is generally solid, and comprises open-cell foam. The occluder 140 includes an annular extension flange 148 projecting radially outwardly and received between the lower edge of the foam wall 110, and the region 112 of the faceplate to which pressure is applied. The foam wall 110 may be relatively non-compressible or stiffly compressible compared to the foam material of the occluder 140.

When the cap 98 is secured to the faceplate 10, the foam wall 110 may compress the extension flange 148, to apply pressure to the region 112 of the faceplate 10. In addition, the force applied to the extension flange 148 by the foam wall 110 may tend to urge the foam stoma occluder against the surface of the stoma 22. The foam stoma occluder is preferably soft to provide a comfortable fit against the stoma 22.

The foam stoma occluder 140 may be of open cell foam to allow flatus from the stoma 22 to pass through the occluder 140 and to reach the foam wall 110. The foam wall 110 also permits the passage of gas therethrough, allowing the gas to reach the collection volume 104, and to vent through the one or more flatus vents 106.

Embodiment 18

Figure 20:
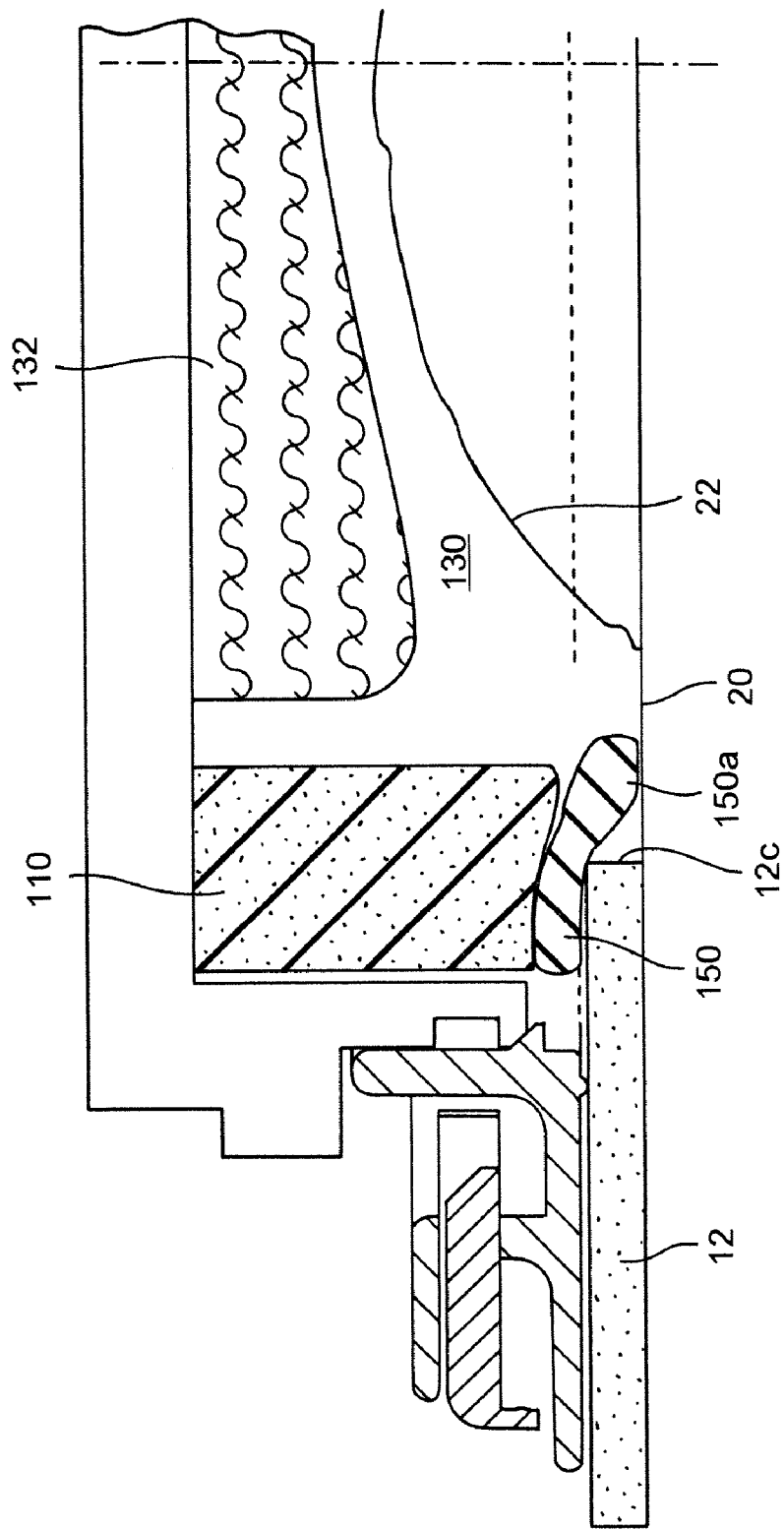
FIG. 20 is a schematic cross-section through part of an eighteenth embodiment of a controlled ostomy discharge device shown on the body.

Referring to FIG. 20, the eighteenth embodiment is similar to the thirteenth and fourteenth embodiments. In the present embodiment, the stoma 22 is not directly occluded by a contacting surface. The appliance may use a faceplate similar to that of the eighth embodiment. The confinement region 130 defined by the foam wall 110 may optionally contain an absorbent member 132 to at least partly fill the confinement region and/or to absorb liquid body waste.

In the present embodiment, the elastomeric sealing member 18 may take the form of a gasket 150. The gasket 150 may be of foam. The gasket is preferably non-permeable. For example, the gasket 150 may comprise closed-cell foam and/or may include impermeable skinned surfaces. The gasket 150 may be separate from the foam wall 110, or the gasket 150 may be joined to, or integrally formed with, the foam wall 110.

The gasket 150 may serve to seal an inner peripheral edge 12c of the adhesive member 12 against contact by body waste excreted by the stoma 22 and collecting in the confinement region 130. At least a portion 150a of the gasket 150 may contact the peristomal skin 20. The gasket 150 may partly overlap the edge 12c of the adhesive member 12 (as illustrated in FIG. 19), or the gasket 150 may entirely bear against the peristomal skin 20.

Embodiment 19

Figure 21:
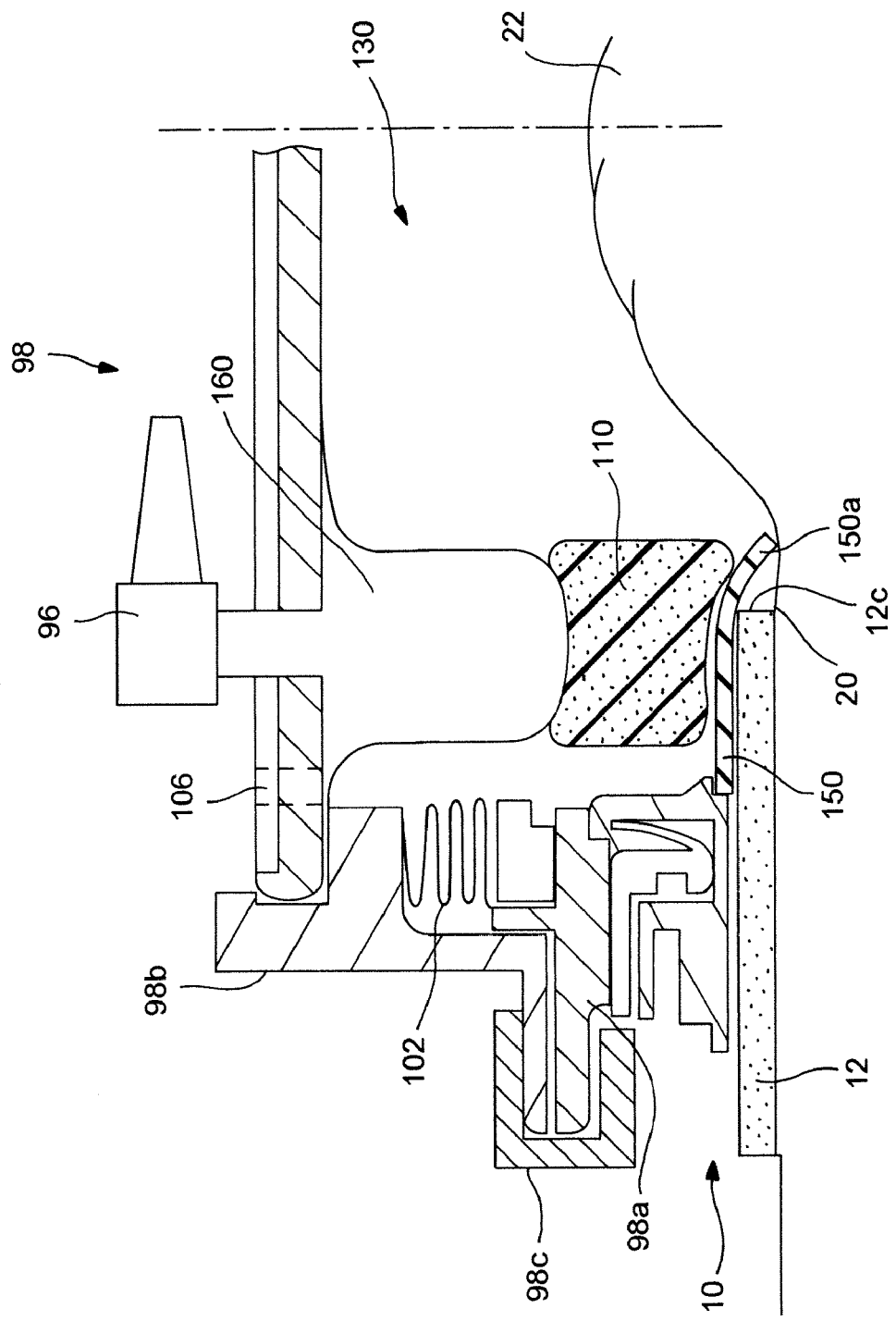
FIG. 21 is a schematic cross-section through part of a nineteenth embodiment of a controlled discharge device shown on the body.

Referring to FIG. 21, the nineteenth embodiment is similar to the eighteenth embodiment, except for the configuration of the confinement volume seal. In FIG. 20, the foam wall 110 does not extend the entire height of the cap. Instead, an inflatable confinement member 160 is disposed on the underside of the cap to bear on the foam wall 110. The confinement member 160 may be generally annular or toroidal and, in the example illustrated, has a width approximately equal to that of the foam wall 110. The confinement member 160 is configured such that it does not apply a force directly to the stoma 22. As in the eighteenth embodiment, the elastomeric sealing member is in the form of a gasket 150 that overlaps the inner edge 12c of the adhesive pad 12. A portion 150c of the gasket may bear against the peristomal skin 20. In this embodiment, the gasket 150 may be configured not to apply a sealing pressure directly to the stoma 22.

The confinement member 160 may be inflated via an inflation port 96, by means of a suitable pump (not shown). The pump may be incorporated into the appliance, or it may be a separate item. The inflation pressure within the confinement member 160 determines the strength of the confinement volume seal relative to the parts 98a and 98b of the cap 98, and the force with which the gasket 150 is pressed against the adhesive pad 12 and/or against the peristomal skin 20. The pressure may also control the degree to which the foam wall 110 is compressed, which might affect the properties of the foam member 110 in separating flatus while containing solid and liquid stomal discharge. As depicted schematically by numeral 106, the region between the collector 102 and the foam wall 110/confinement member 160 may be vented to allow the escape of flatus that has passed through the foam wall 110. A deodorising filter (not shown) may be incorporated to deodorise the flatus.

Embodiment 20

Figure 22:
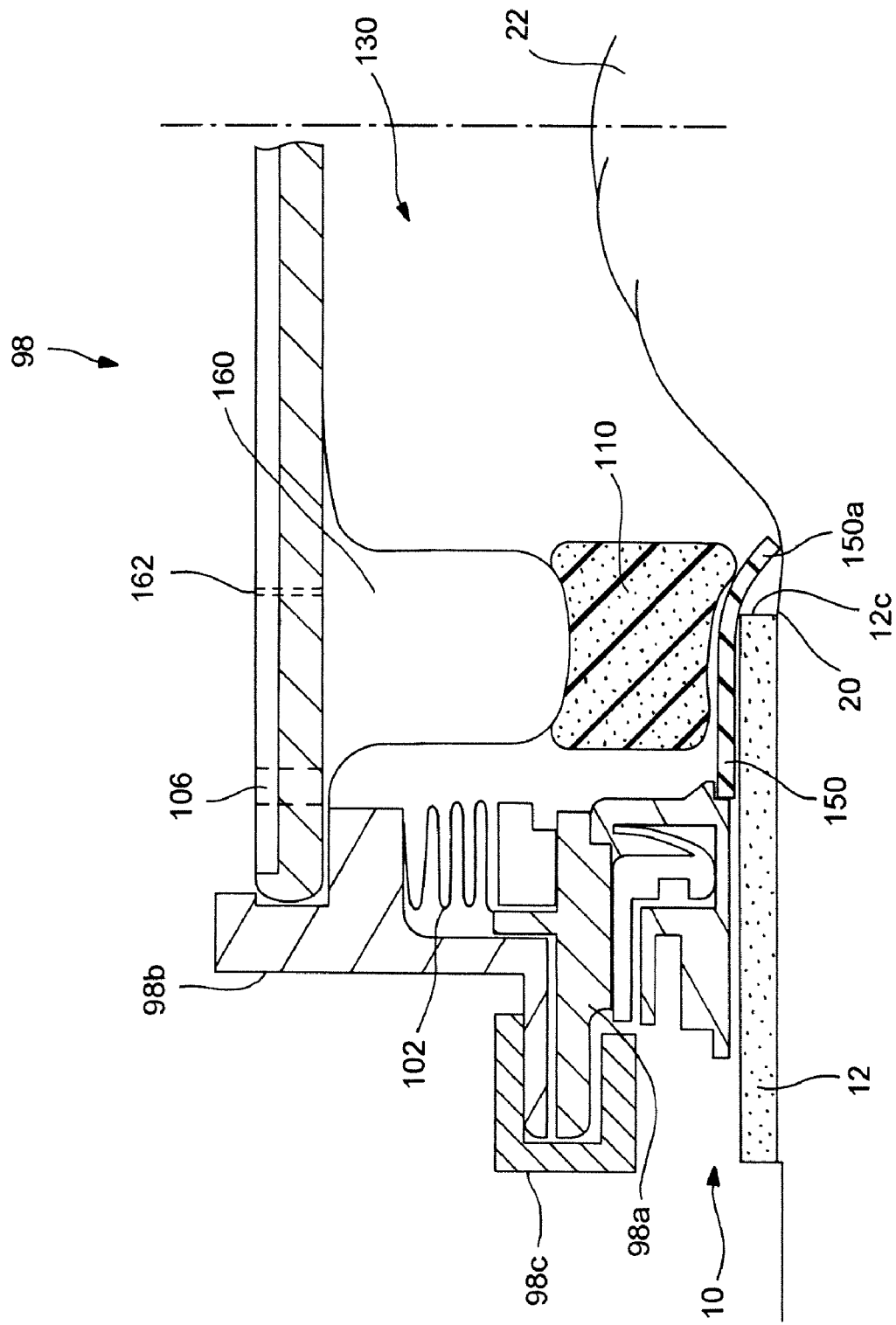
FIG. 22 is a schematic cross-section through part of a twentieth embodiment of a controlled discharge device shown on the body.

Referring to FIG. 22, the twentieth embodiment is very similar to the nineteenth embodiment. The main difference lies in the manner in which the confinement member 160 is inflated. In the previous embodiment, an inflation port 96 is provided to allow the ostomate to inflate the confinement member 160 to a desired pressure. In the present embodiment, the confinement member is pre-inflated, for example, during manufacture of the ostomy appliance. A small port 162 may be provided in the cap 98 to allow for inflation during manufacture. The port 162 may be sealed by a plug (not shown) to prevent escape of the inflation fluid.

In this embodiment, the inflation pressure of the confinement member 160 may be predetermined by the manufacturer. This can help avoid differences in performance caused by under- or over-inflation of the confinement member 160 by an ostomate. It also avoids the inconvenience to the ostomate of having to inflate the confinement member 160, and avoids the inconvenience and expense of providing the user with a dedicated inflation pump.

In this embodiment, the volume of the confinement member 160 may generally be fixed by the design of the cap 98. The confinement member 160 does not bear against the stoma 22, and so the volume of the confinement member 160 may not be affected by the size and shape of the stoma 22. Since the volume may generally be fixed, then the inflation pressure within the confinement member 160 may be predictable when the appliance is worn on the body. Should adjustment of the inflation pressure be desired, then the pressure may be varied by changing the thickness of the foam member 110 and/or the gasket 150, or some other dimension. A range of ostomy appliances may be manufactured with different models inflated to different inflation pressures. The ostomate may select (or be prescribed) a respective model having an inflation pressure to suit his or her personal characteristics.

Embodiment 21

Figure 23:
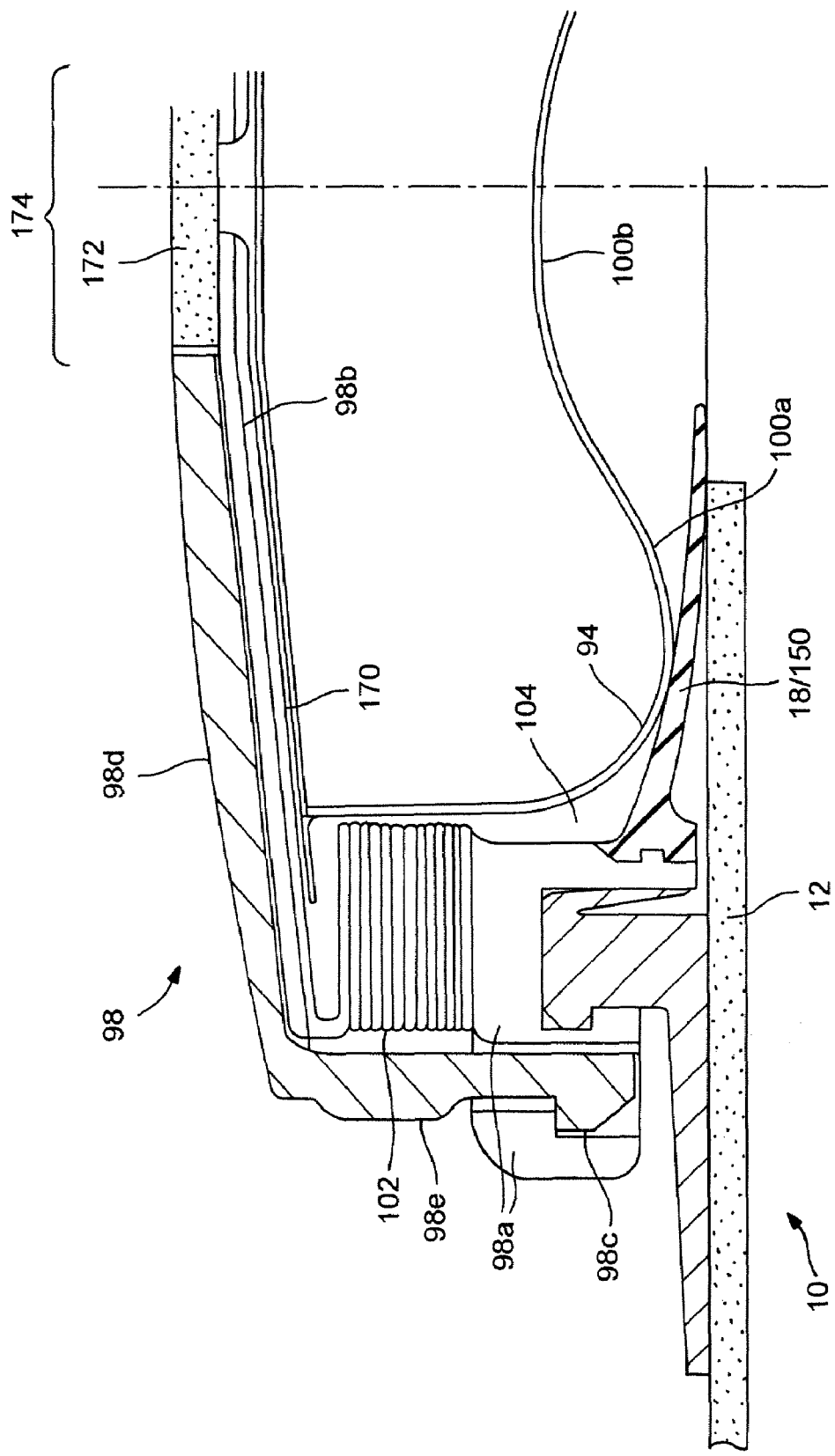
FIG. 23 is a schematic cross-section through part of a twenty first embodiment of a controlled discharge device.

Referring to FIG. 23, the twenty first embodiment is very similar to the eighth embodiment. One difference lies in the manner in which the inflatable balloon 94 is inflated. In the eighth embodiment, an inflation port 96 is provided to allow the ostomate to inflate the inflatable balloon 94 to a desired pressure. In the present embodiment, the inflatable balloon 94 is pre-inflated, for example, during manufacture of the ostomy appliance. A small port (not shown) may be provided in the cap 98 to allow for inflation during manufacture. The port may be sealed by a plug (not shown) to prevent escape of the inflation fluid.

In a similar manner to the twentieth embodiment, pre-inflation of the balloon 94 provides advantages in simplicity and convenience of use, and avoids the need for the user or the appliance to carry a dedicated inflation pump.

In the present embodiment, the balloon 94 may be configured to contact the stoma 22. The shape and volume of the balloon 94 may therefore vary in use, depending on the shape and size of the individual's stoma 22. Such variations in volume may affect the pressure within the balloon 94, and hence affect the seal pressure of the balloon 94 against the stoma 22.

A range of appliances may be produced having different initial inflation pressures. The ostomate may select (or be prescribed) a model having a particular initial inflation pressure to suit his or her stoma. Additionally, or alternatively, the volume of the balloon 94 may be controlled by a characteristic of the cap 98. For example, the characteristic may a distance between the faceplate 10 (or the first part 98a of the cap 98), and a rear surface (98b/98d) on which the balloon 94 is supported. This distance may be controlled by a dimension of the cap 98. A range of caps 98 may be produced having different characteristic dimensions for controlling the volume of the balloon 94, and the ostomate may select (or be prescribed) a suitable model for his or her stoma.

In the example illustrated, the balloon 94 is supported by the second cap part 98b that is coupled to the collector 102. The second cap part 98b is coupled to an outer cap cover 98d to depend from the cover 98d. The cover 98d has a skirt or sidewall 98e that extends towards the faceplate 10, and is releasably secured to the first cap part 98a by the releasable connection 98c. In this example, the releasable connection 98c is a mechanical catch. The height of the sidewall 98e may determine the "height" of the second cap part 98 above the faceplate 10, and hence can control the extent to which the balloon 94 is pressed against the stoma 22. A range of outer covers 98d having different sidewall heights 98e may be produced. An ostomate may choose (or be prescribed) an appliance having a particular sidewall height to suit his or her stoma.

Additionally, or alternatively, the cap 98 may include an adjustment mechanism for adjusting the height of the second cap part 98b relative to the faceplate 10. For example, such an adjustment mechanism may adjust the position of the second cap part 98b relative to the outer cap cover 98d, and/or the position of the outer cap cover 98d relative to the first cap part 98a. For example, a threaded or ramp connection may be used to control axial displacement according to a rotational position. A threaded example is illustrated in Embodiment 23.

Additionally, or alternatively, one or more spacers (not shown) may be provided for adjustment of the relative positioning of the balloon 94 or surfaces abutting or supporting the balloon 94.

Additionally, or alternatively, the thickness (e.g. height) of the sealing member 18 (and/or of a foam wall (not shown) if provided) may be varied to affect the volume of the balloon 94 and hence affect the inflation pressure of the balloon 94. For example, a range of sealing members of different thickness, and/or a range of foam walls of different thickness (e.g., height) may be provided to allow an ostomate to select a suitable size to suit his or her stoma. Such sealing members or foam wall ranges may either be pre-installed in a range of different caps 98, or they may be installable by the ostomate in a standard cap 98 to customise the cap 98 to suit his or her stoma.

Flatus may vent from the region 104 between the balloon 94 and the collector 102 by passing through one or more vent channels 170 between the second cap part 98b and the outer cap cover 98d. The channels may, for example, be defined by one or more contours of the upper surface of the second cap part 98b and/or the lower surface of the outer cap cover 98d. The channels 170 may be generally narrow in at least one dimension to obstruct the passage of solid stomal discharge in the channels 170. A deodorising filter 172 may be provided at a vent aperture 174 of the cap 98, in communication with the channels 170, such that flatus venting from the cap 98 passes through the deodorising filter 172 in order to pass to the outside environment.

In the example shown in FIG. 22, the balloon 94 may have a contoured profile, including a peripheral annular projecting portion 100a and central recess or depression 100b contoured to an approximate shape of a stoma.

Embodiment 22

Figure 26:
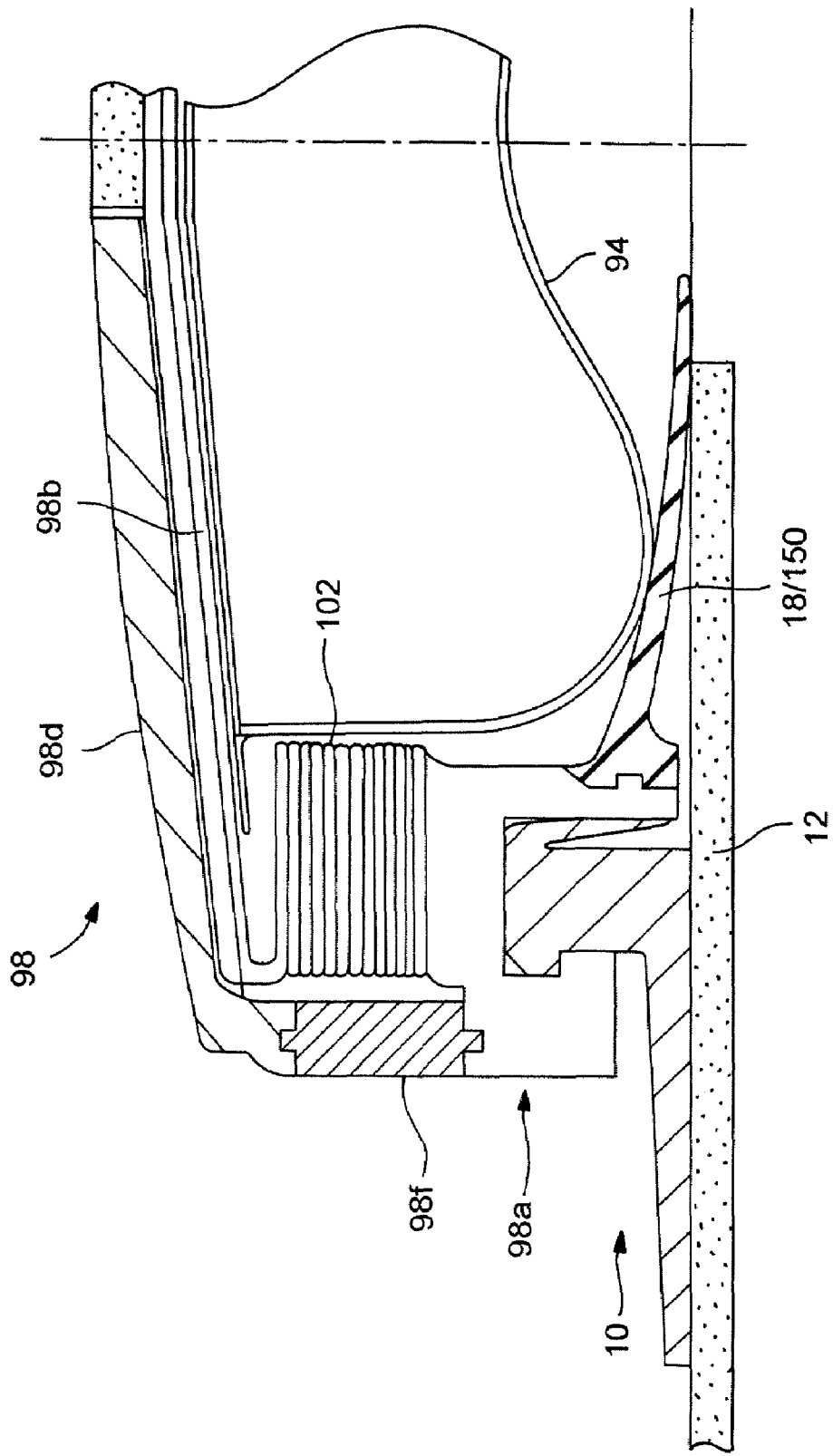
FIG. 26 is a schematic cross-section through part of a twenty second embodiment of a controlled discharge device.

Referring to FIG. 26, the twenty second embodiment is very similar to the twenty first embodiment. The main difference lies in the implementation of the sidewall 98e for the outer cap cover 98d, and of the releasable connection 98c to the first cap part 98a. In the present embodiment, the sidewall 98e and the releasable connection 98c may be formed by an annular spacer or segment 98f that is arranged between an upper part of the outer cap cover 98d, and the first cap part 98a. The annular segment 98f may include a releasable connection (for example, a frangible connection) to one or both of the outer cap cover 98d or the first cap part 98a. The length (or "height") of the annular segment 98f may determine the height of the outer cap cover 98d and the second cap part 98b relative to the first cap part 98a, and hence may control the volume of the balloon 94.

When the ostomate desires to discharge from the stoma, the ostomate releases the outer cover part 98d, which removes the balloon 94 from sealing engagement, and allows distention of the collector 102.

Embodiment 23

Figure 27:
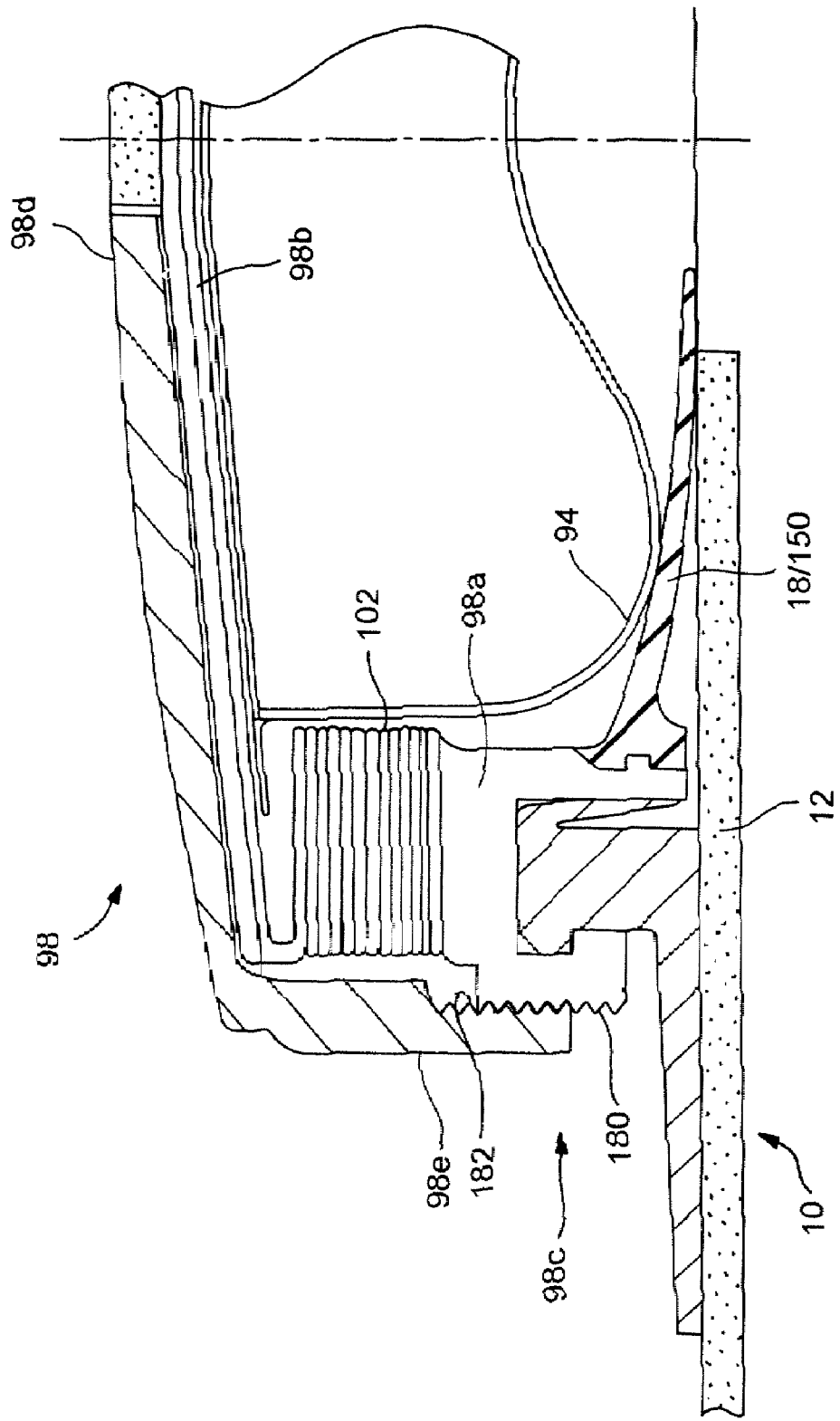
FIG. 27 is a schematic cross-section through part of a twenty third embodiment of a controlled discharge device.

Referring to FIG. 27, the twenty third embodiment is similar to the twenty first embodiment. The main difference lies in the implementation of the releasable connection 98c between the outer cap cover 98d and the first cap part 98a. In the present embodiment, a screw threaded connection is formed between a first screw thread 180 on the first cap part 98a, and a second screw thread 182 on the side wall 98e of the outer cap cover 98d. An ostomate can adjust the volume (and hence pressure) of the balloon 94 by rotation of the outer cap cover 98d relative to the first cap part 98a. Rotation in one direction (e.g., counterclockwise) may increase the distance of the outer cap cover 98d (and hence the second cap part 98b) from the first cap part 98a. Rotation in the other direction (clockwise) may reduce the distance of the outer cap cover 98d (and hence the second cap part 98b) from the first cap part 98a.

When the ostomate desires to discharge from the stoma, the ostomate completely unscrews the outer cap cover 98d to separate the outer cap cover 98d from the first cap part 98a.

The second cap part 98b may be secured to the outer cap cover 98d for rotation therewith. Alternatively, the outer cap cover 98d may be rotatable relative to the second cap part 98b. The second cap part 98b may remain in a fixed rotational orientation with respect to the first cap part 98a.

In a modified form, the threaded connection may be between the outer cap cover 98d and the second cap part 98b. Rotation of the outer cap cover 98d may then generate relative movement of the second cap part 98b either towards or away from the outer cap cover 98d.

Embodiment 24

Figure 28:
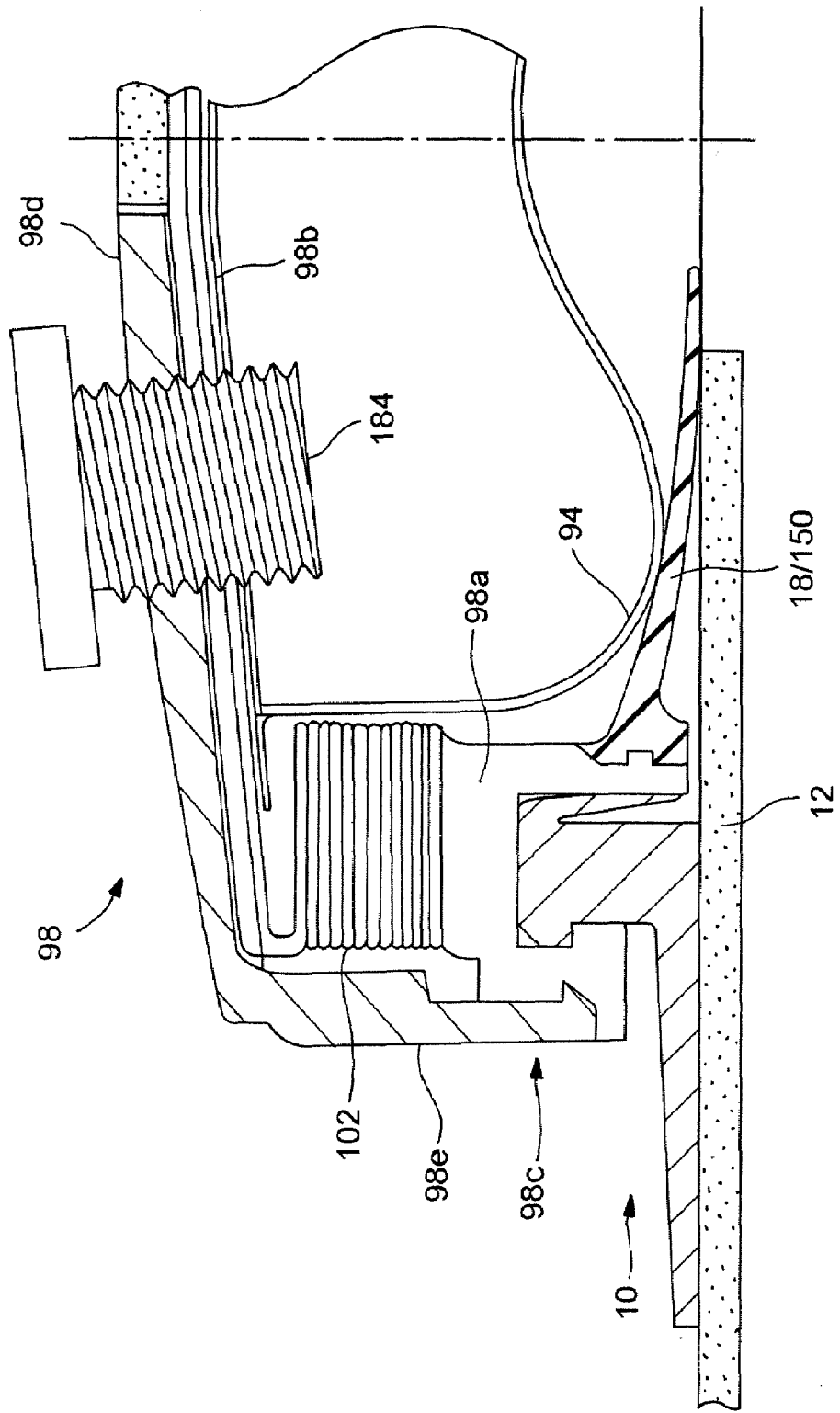
FIG. 28 is a schematic cross-section through part of a twenty fourth embodiment of a controlled discharge device.

Referring to FIG. 28, the twenty fourth embodiment is similar to the twenty first embodiment. The main difference lies in the addition of an adjuster projection 184 that projects inwardly from the second cap part 98b and/or the outer cap cover 98d. The adjuster projection 184 may press on the balloon 94 to increase the pressure of the balloon 94 by reducing the volume occupied by the balloon 94.

In the present embodiment, the adjuster projection 184 may be screw threaded to permit the degree of protrusion of the projection 184 to be varied. The adjuster projection 184 may extend through the second cap part 98b and/or the outer cap cover 98d to permit external adjustment.

The tip of the adjuster projection 184 may be shaped to have a smooth profile. The profile may reduce the risk of damage to the balloon 94. Additionally, or alternatively, one or more protection members (not shown) may be disposed around or near the adjuster projection 184, to protect the balloon 94 from the projection 184.

Embodiment 25

Figure 24:
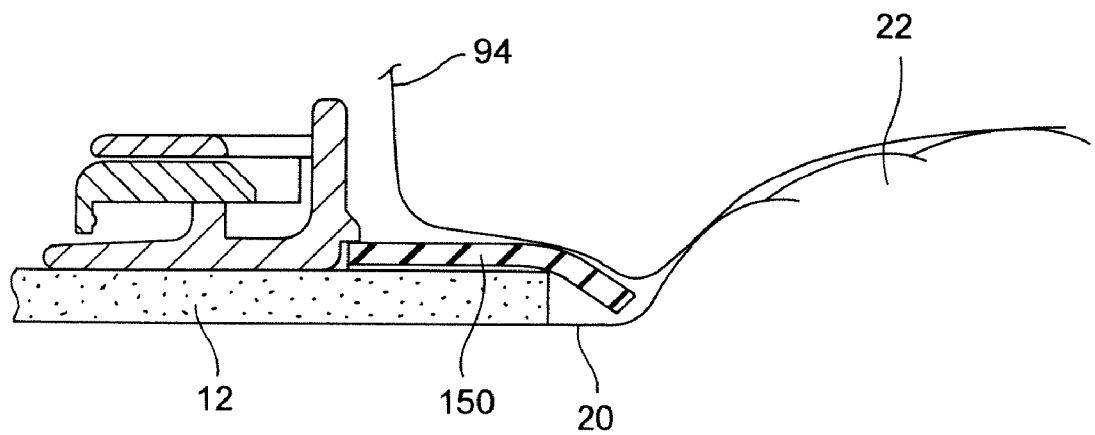
FIGS. 24 and 25 are schematic partial views illustrating alternative seal configurations for the twenty first embodiment of the invention.
Figure 25:
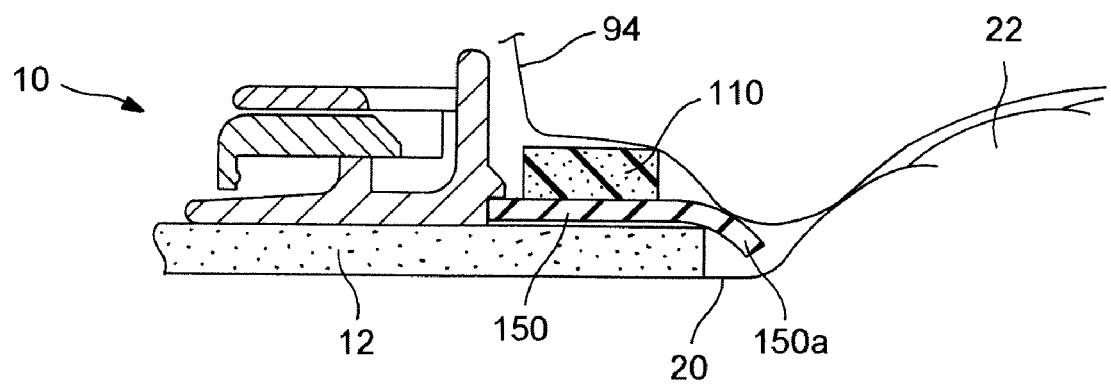

FIGS. 24 and 25 illustrate alternative configurations for the sealing member 18/150 of the twenty first to twenty fourth embodiments. FIG. 24 illustrates the sealing member in the form of a gasket 150 as described in more detail in the eighth and eighteenth embodiments. In FIG. 24, the balloon 94 may be pre-inflated, or it may be inflatable by the ostomate using a suitable inflation pump.

FIG. 25 is similar to FIG. 24, but includes an annular foam wall 110 arranged on top of the gasket 150. The foam wall 110 is permeable to allow flatus to pass therethrough, while obstructing the passage of solid or liquid body waste. The foam wall 110 may be as described in any of the eleventh to twenty first embodiments. The foam wall 110 and the gasket 150 may be secured or formed together as a composite member, or the foam wall 110 and the gasket 150 may be separate or separable elements.

Combinations of the features of the individual controlled discharge devices of embodiments nine to twenty five are also envisaged.

It will also be appreciated that the foregoing description is merely illustrative of preferred forms of the invention, and that many modifications, improvements and equivalents may be used without departing from the scope and/or principles of the invention. Accordingly, the claims are to be construed to encompass all such modifications, improvements and equivalents.

The invention claimed is:

1. An ostomy appliance comprising:
   adhesive means secured to the ostomy appliance for removably adhering the ostomy appliance to an ostomate's skin, said adhesive means including an adhesive member having an inner periphery and a stomal aperture;
   sealing and protecting means for sealing the inner periphery of the adhesive member around the stomal aperture and protecting the adhesive member from contact by stomal discharge, said sealing and protecting means including a pressurizable elastometric sealing member having an outer surface facing away from the ostomate's skin, said sealing member comprising foam;
   pressure producing and applying means for producing pressure from a source external to a stoma and applying said externally sourced pressure directly or indirectly to said outer surface of said pressurizable elastometric sealing member and urging said sealing member towards the skin, said producing and applying means including a cap on said adhesive member defining a space therebetween containing at least a portion of said pressure producing and applying means; and
   a non-entrant stoma occluder at least partly within the cap for occluding the stoma externally.

2. The ostomy appliance according to claim 1, wherein the non-entrant stoma occluder comprises a stoma occluding surface configured, in use, to apply a force directly or indirectly to the elastomeric sealing member, to urge said stoma contacting surface towards the stoma to form the seal.

3. The ostomy appliance according to claim 2, wherein the elastomeric sealing member is configured to be at least partly sandwiched between the stoma and the stoma occluding surface as a gasket.

4. The ostomy appliance according to claim 1, wherein the elastomeric sealing member is substantially non-moldable.

5. The ostomy appliance according to claim 4, wherein the elastomeric sealing member has a stoma engaging surface, and wherein the stoma engaging surface is configured, at least in use, to have or adopt a generally closed-loop concave configuration, to at least partly cup the stoma.

6. The ostomy appliance according to claim 4, wherein the stoma contacting surface of the sealing member is tapered or flared to define said concave configuration.

7. The ostomy appliance according to claim 4, wherein the stoma engaging surface of the sealing member is generally frusto-conical.

8. The ostomy appliance according to claim 1, wherein the elastomeric sealing member is non-moldable and includes a peristomal region, and further comprising a shape defining member for directly or indirectly applying pressure through at least the peristomal region of the sealing member to the ostomate's skin.

9. The ostomy appliance according to claim 8, wherein the shape defining member is configured not to apply pressure directly to the stoma surface of the elastomeric sealing member.

10. The ostomy appliance according to claim 8, wherein the shape defining member is configured to apply pressure to the stoma engaging surface of the elastomeric sealing member.

11. The ostomy appliance according to claim 8, wherein the shape defining member comprises a resilient member.

12. The ostomy appliance according to claim 8, wherein the shape defining member is configured to define a generally convex shape in a peristomal region.

13. The ostomy appliance according to claim 8, wherein the shape defining member is integrally formed with the elastomeric sealing member.

14. The ostomy appliance according to claim 1, wherein the sealing member comprises a synthetic material.

15. The ostomy pouch according to claim 1, wherein the stoma occluder comprises an inflatable member.

16. The ostomy appliance of claim 1, further comprising a wall of closed loop configuration arranged at least peristomally to define a confinement region for confining any solid waste excreted from the stoma, the wall comprising open cell foam for permitting flatus to vent therethrough.

17. The ostomy appliance according to claim 16, wherein the appliance further comprises a first member attachable directly or indirectly to an ostomate's skin and having a stomal aperture, and a cover releasably securable directly or indirectly to the first member.

18. The ostomy appliance according to claim 17, wherein the wall comprises resiliently compressible foam that, when the cover is secured to the first member, is compressed to seal said confinement region between the first member and the cover.

19. An ostomy appliance comprising:
  adhesive means secured to the ostomy appliance for removably adhering the ostomy appliance to an ostomate's skin, said adhesive means including an adhesive member having an inner periphery and a stomal aperture;
  sealing and protecting means for sealing the inner periphery of the adhesive member around the stomal aperture and protecting the adhesive member from contact by stomal discharge, said sealing and protecting means including a non-moldable, pressurizable elastometric sealing member having an outer surface facing away from the ostomate's skin and a peristomal region;
  pressure producing and applying means for producing pressure from a source external to a stoma and applying said externally sourced pressure directly or indirectly to said outer surface of said pressurizable elastometric sealing member and urging said sealing member towards the skin, said producing and applying means including a cap on said adhesive member defining a space therebetween containing at least a portion of said pressure producing and applying means;
  a non-entrant stoma occluder at least partly within the cap for occluding the stoma externally; and
  a shape defining member for directly or indirectly applying pressure through at least the peristomal region of the sealing member to the ostomate skin, said shape defining member comprising a resilient member.

20. An ostomy appliance comprising:
  adhesive means secured to the ostomy appliance for removably adhering the ostomy appliance to an ostomate's skin, said adhesive means including an adhesive member having an inner periphery and a stomal aperture;
  sealing and protecting means for sealing the inner periphery of the adhesive member around the stomal aperture and protecting the adhesive member from contact by stomal discharge, said sealing and protecting means including a non-moldable, pressurizable elastometric sealing member having an outer surface facing away from the ostomate's skin and a peristomal region;
  pressure producing and applying means for producing pressure from a source external to a stoma and applying said externally sourced pressure directly or indirectly to said outer surface of said pressurizable elastometric sealing member and urging said sealing member towards the skin, said producing and applying means including a cap on said adhesive member defining a space therebetween containing at least a portion of said pressure producing and applying means;
  a non-entrant stoma occluder at least partly within the cap for occluding the stoma externally; and
  a shape defining member for directly or indirectly applying pressure through at least the peristomal region of the sealing member to the ostomate skin, wherein said shape defining member is configured to define a generally convex shape in a peristomal region.

21. An ostomy appliance comprising:
  adhesive means secured to the ostomy appliance for removably adhering the ostomy appliance to an ostomate's skin, said adhesive means including an adhesive member having an inner periphery and a stomal aperture;
  sealing and protecting means for sealing the inner periphery of the adhesive member around the stomal aperture and protecting the adhesive member from contact by stomal discharge, said sealing and protecting means including a non-moldable, pressurizable elastometric sealing member having an outer surface facing away from the ostomate's skin and a peristomal region;
  pressure producing and applying means for producing pressure from a source external to a stoma and applying said externally sourced pressure directly or indirectly to said outer surface of said pressurizable elastometric sealing member and urging said sealing member towards the skin, said producing and applying means including a cap on said adhesive member defining a space therebetween containing at least a portion of said pressure producing and applying means;
  a non-entrant stoma occluder at least partly within the cap for occluding the stoma externally; and
  a shape defining member for directly or indirectly applying pressure through at least the peristomal region of the sealing member to the ostomate skin, wherein said shape defining member is integrally formed with said elastomeric sealing member.

* * * * *